US012721880B2

(12) United States Patent
Stossel et al.

(10) Patent No.: US 12,721,880 B2
(45) Date of Patent: Sep. 1, 2026

(54) METHODS AND COMPOSITIONS FOR TREATING FRAILTY

(71) Applicants: BioAegis Therapeutics Inc., Morristown, NJ (US); Timo E. Strandberg, Helsinki (FI); Kerry Maguire, Belmont, MA (US)

(72) Inventors: Thomas P. Stossel, Morristown, NJ (US); Timo E. Strandberg, Helsinki (FI)

(73) Assignees: BioAegis Therapeutics Inc., Morristown, NJ (US); Timo Strandberg, Helsinki (FI)

( * ) Notice: Subject to any disclaimer, the term of this patent is extended or adjusted under 35 U.S.C. 154(b) by 920 days.

(21) Appl. No.: 17/923,168

(22) PCT Filed: May 3, 2021

(86) PCT No.: PCT/US2021/030422
§ 371 (c)(1),
(2) Date: Nov. 3, 2022

(87) PCT Pub. No.: WO2021/225937
PCT Pub. Date: Nov. 11, 2021

(65) Prior Publication Data

US 2023/0158107 A1 May 25, 2023

Related U.S. Application Data

(60) Provisional application No. 63/019,482, filed on May 4, 2020.

(51) Int. Cl.
*A61K 38/17* (2006.01)
*A61P 21/00* (2006.01)

(52) U.S. Cl.
CPC .......... *A61K 38/1709* (2013.01); *A61P 21/00* (2018.01)

(58) Field of Classification Search
None
See application file for complete search history.

(56) References Cited

FOREIGN PATENT DOCUMENTS

| | | | |
|---|---|---|---|
| WO | 2009021360 | A1 | 2/2009 |
| WO | 2009094194 | A2 | 7/2009 |
| WO | 2020257743 | A1 | 12/2020 |

OTHER PUBLICATIONS

Yang et al (OFID, 2017:4 (Suppl 1) Abstract 1519, Session 167).*
Collard, R. M. et al., "Prevalence of frailty in community-dwelling older persons: a systematic review" (2012) J. American Geriatrics Soc., vol. 60, Issue 8, 1487-1492.
Feldt J. et al., "Structure, regulation and related diseases of the actin-binding protein gelsolin" RevMolec Med (2019) 20, e7.
Fried, L., et al., "Frailty in older adults: evidence for a phenotype" (2001) J. Gerontology: Medical Sciences, 56A:3, MI46-MI56.

(Continued)

*Primary Examiner* — Patricia Duffy
(74) *Attorney, Agent, or Firm* — Pierce Atwood LLP; Christopher A. Baxter

(57) ABSTRACT

This invention relates to the assessment of frailty conditions and methods of using gelsolin to treat frailty conditions.

16 Claims, 4 Drawing Sheets

(56) References Cited

OTHER PUBLICATIONS

Gupta, A, et al., "Analgesic and Anti-Inflammatory Properties of Gelsolin in Acetic Acid Induced Writhing. Tail Immersion and Carrageenan Induced Paw Edema in Mice" (2015) PLoSOne, 10: p. 0135558.
Ha Y.C. et al., "Hand grip strength measurement in different epidemiologic studies using various methods for diagnosis of sarcopenia: a systematic review" EurGeriatr Med. 9, 277-288 (2018).
Huang L-f et al. (2011) "Reduction of Plasma Gelsolin Levels Correlates with Development of Multiple Organ Dysfunction Syndrome and Fatal Outcome in Burn Patients." PLoS One 6(11): e25748. doi:10.1371/journal.pone.0025748.
International Search Report and Written Opinion from the International Searching Authority dated Dec. 8, 2021 from corresponding International Patent Application No. PCT/US2021/030422 Filed on May 3, 2021.
Kaneva, M., et al., "Identification of Novel Chondroprotective Mediators in Resolving Inflammatory Exudates." (2017) J Immunol, 7: p. 2876-2885.
Kim, N. H. et al., "Weight-adjusted waist index reflects fat and muscle mass in the opposite direction in older adults" Age Ageing afaa208 (2020).
Kulakowska et al. "Depletion of Plasma Gelsolin in Patients with Tick-Borne Encephalitis and Lyme Neuroborreliosis" (2011) Neurodegenerative Dis. 8:375-380.
Kulakowska, A. et al. "Hypogelsolinemia, a disorder of the extracellular actin scavenger system, in patients with multiple sclerosis" (2010) BMC Neurology 10:107.
Lee PS & Stossel TP "Relationship of Plasma Gelsolin Levels to Outcomes in Critically Ill Surgical Patients" (2006) Annals of Surgery, 243(3):399-403.
Lee PS et al. "Plasma Gelsolin and Circulating Actin Correlate with Hemodialysis Mortality" (2009) J. American Society of Nephrology: JASN. 20(5):1140-8.
Lee PS et al. "Plasma Gelsolin Depletion and Circulating Actin inSepsis—A Pilot Study" (2008) PLOS One 3:11, 3712.
Osborn TM et al. "Decreased levels of the gelsolin plasma isoform in patients with rheumatoid arthritis" (2008) Arthritis Research & Therapy 10(5):R117.
Patel, S. S. et al., "Serum creatinine as a marker of muscle mass in chronic kidney disease: results of a cross-sectional study and review of literature" J.Cachexia Sarcopenia Muscle 4:19 (2013).
Peddada, N., et al., "Plasma gelsolin: a general prognostic marker of health." Med Hypotheses, 2012. 78: p. 203-210.
Posey, Celeste et al. (2000) "Failure of gelsolin overexpression to regulate lymphocyte apoptosis" Blood vol. 95, No. 11, p. 3483-3488.
Qian-Li Xue: "The Frailty Syndrome: Definition and Natural History", Clinics in Geriatric Medicine., vol. 27, No. 1, Feb. 1, 2011 (Feb. 1, 2011).
Searle, S.D. et al., "A standard procedure for creating a frailty index" BMC Geriatr. Sep. 30, 2008;8:24. doi: 10. I186/1471-2318-8-24.
Self W. H. et al., "Low Admission Plasma Gelsolin Concentrations Identify Community-acquired Pneumonia Patients at High Risk for Severe Outcomes" Clin Infect Dis. 69(7): 1218-1225 (2019).
Sirola J, et al., "Definition of frailty in older men according to questionnaire data (RAND-36/SF-36): The Helsinki Businessmen study" (2011) J Nutr Health Aging; 15 :783-787.
Song X, et al., "Prevalence and 10-year outcomes of frailty in older adults in relation to deficit accumulation" (2010) J Am Geriatr Soc.58(4):681-7.
Soysal, et al., "Inflammation and frailty in the elderly: A systematic review and meta-analysis" (2016) Ageing Res Rev, 3: p. 1-8.
Strandberg et al., "Cohort Profile: The Helsinki Businessmen Study (HBS)" (2016) International J. of Epidemiology vol. 45, Issue 4 pp. 1074-1074h, doi.org/10.1093/ije/dyv310.
Studenski S. et al., "Gait Speed and Survival in Older Adults" JAMA 305(1), 50-58 (2011).
Tager, Andrew M. et al, (2008) "The lysophosphatidic acid receptor LPA1 links pulmonary fibrosis to lung injury by mediating fibroblast recruitment and vascular leak" Nature Medicine, vol. 14, No. 1, p. 45-54.
Yang Zhiping et al: "Delayed Administration of Recombinant Plasma Gelsolin Improves Survival in a Murine Model of Penicillin-Susceptible and Penicillin-Resistant Pneumococcal Pneumonia", Journal of Infectious Diseases, vol. 220, No. 9, Sep. 26, 2019 (Sep. 26, 2019), pp. 1498-1502.

* cited by examiner

Hazard Function
0.0
0.1
0.2
0.3
0.4
2011
2012
2013
2014
2015
2016
Cohort mortality (2011-2016)

METHODS AND COMPOSITIONS FOR TREATING FRAILTY

RELATED APPLICATIONS

This application claims priority under 35 U.S.C. § 371 to international application number PCT/US2021/030422, filed May 3, 2021, and claims the benefit under 35 U.S.C. § 119(e) of U.S. Provisional application Ser. No. 63/019,482, filed May 4, 2020, the disclosure of each of which is incorporated by reference herein in its entirety.

FIELD OF THE INVENTION

The invention, in some aspects, relates to compositions and methods for treating frailty conditions in a subject.

BACKGROUND

Frailty is a syndrome characterized by reduced physical endurance and increased susceptibility to endogenous and exogenous stressors [Song X, et al., (2010) J Am Geriatr Soc. 58(4):681-7]. Frailty predisposes affected individuals to various disabilities, increases their susceptibility to disease, trauma, and hospitalization and is a predictor of mortality [Fried, L., et al., (2001) J. Gerontology: Medical Sciences, 56A:3, M146-M156; Song X, et al., (2010) J Am Geriatr Soc. 58(4):681-7; Sirola J, et al., (2011) J Nutr Health Aging. 15:783-787]. Phenotypic frailty is often defined by five criteria originally described by Fried and colleagues: unintentional weight loss predominantly due to loss of muscle tissue, slow walking pace, exhaustion, weak grip strength, and physical inactivity [Fried, L., et al., (2001) J. Gerontology: Medical Sciences, 56A:3, M146-M156]. The presence of 3-5 Fried criteria denotes frailty, and the presence of 1-2 denotes prefrailty. Frailty is not exclusive to aging, but is a prevalent age-related condition. Epidemiological studies have established the prevalence of frailty as 10% among persons aged 70 years and over [Collard, R. M. et al., (2012) J. American Geriatrics Soc., Vol. 60, Issue 8, 1487-1492], but the prevalence increases steeply with age; prefrailty can be identified in half of older cohorts.

Because loss of muscle mass is a characteristic of frailty, frailty can overlap with a syndrome defined as sarcopenia. Patients afflicted with sarcopenia exhibit many of the same signs and symptoms affecting frailty patients. The high prevalence of frailty and sarcopenia represents a serious clinical and economic burden on society, which is exacerbated by a lack of efficacious therapeutics for these conditions.

SUMMARY OF THE DISCLOSURE

According to an aspect of the invention, a method for treating a frailty condition in a subject is provided, the method including administering to a subject in need of a frailty condition treatment, an effective amount of a gelsolin agent to treat the frailty condition in the subject. In some embodiments, a characteristic of the frailty condition is weight loss, exhaustion, weakness, and/or physical inactivity. In some embodiments, characteristic of the frailty condition in the subject include one or more of: weight loss, exhaustion, weakness, and physical inactivity. In some embodiments, the subject exhibits at least 1, 2, 3, or 4 of the frailty characteristics. In some embodiments, the subject exhibits 1 or 2 of the frailty characteristics. In some embodiments, the subject exhibits 3 or 4 of the frailty characteristics. In some embodiments, the method also includes determining a status of one or more of the characteristics of the frailty condition exhibited by the subject. In some embodiments, the status of the one or more characteristics is determined at 1, 2, 3, 4, 5, 6, 7, 8, 9, 10, or more different time points. In some embodiments, the status of the one or more characteristics is determined at one of more of: (1) a time prior to administering the gelsolin agent; and (2) a time after administering the gelsolin agent. In some embodiments, the method also includes comparing the determined status of the one or more characteristics in the subject with a control status of the one or more frailty characteristics, respectively, wherein an improvement in the determined status of at least one of the characteristics in the subject compared to the control status of the characteristic, indicates effectiveness of the administered gelsolin in the subject. In some embodiments, the control status includes the status of the characteristic in the subject prior to the administering of the gelsolin agent. In some embodiments, administering the gelsolin agent increases the subject's likelihood of survival compared to a control likelihood of survival. In some embodiments, the control likelihood of survival is a likelihood of survival in the absence of administering the gelsolin agent. In some embodiments, the subject's likelihood of survival following administration of the gelsolin agent is at least 1%, 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, or 200% higher than the control likelihood of survival. In some embodiments, the subject's likelihood of survival following administration of the gelsolin agent is between 1% and 100%, 10% and 100%, 50% and 100%, 50% and 200%, 100% and 200%, 20% and 100%, 1% and 150%, and/or 1% and 200% higher than the control likelihood of survival. In some embodiments, the subject has one or more symptoms of: muscle wasting, cachexia, physical injury, impaired locomotion, and decreased physical stability. In some embodiments, the method also includes determining a status of one or more of: muscle wasting, cachexia, physical injury, impaired locomotion, and decreased physical stability in the subject. In some embodiments, the status is determined at 1, 2, 3, 4, 5, 6, 7, 8, 9, 10, or more different time points. In some embodiments, the status is determined at one of more of: (1) a time prior to administering the gelsolin agent; and (2) a time after administering the gelsolin agent. In some embodiments, administering the gelsolin agent to the subject improves the status of one or more of muscle wasting, cachexia, physical injury, impaired locomotion, and decreased physical stability in the subject compared to a control status of muscle wasting, cachexia, physical injury, impaired locomotion, and decreased physical stability, respectively. In some embodiments, following administration of the gelsolin agent to the subject, the determined status of one or more of muscle wasting, cachexia, physical injury, impaired locomotion, and decreased physical stability in the subject improves by at least 1%, 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, or 200% compared to the control status of muscle wasting, cachexia, physical injury, impaired locomotion, and decreased physical stability, respectively. In some embodiments, following administration of the gelsolin agent to the subject, the determined status of one or more of muscle wasting, cachexia, physical injury, impaired locomotion, and decreased physical stability in the subject improves by about 1%, 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, or 200% compared to the control status of muscle wasting, cachexia, physical injury, impaired locomotion, and decreased physical stability, respectively. In some embodiments, following administration of the gelsolin agent to the subject, the determined status of one or more of muscle wasting, cachexia, physical injury, impaired locomotion, and decreased physical stability in the subject improves by between 1% and 200%, 10% and 100%, 1% and 100%, 5% and 100%, 50% and 100%, 50% and 200%, 100% and 200%, 20% and 100%, and/or 1% and 150% compared to the control status of muscle wasting, cachexia, physical injury, impaired locomotion, and decreased physical stability, respectively. In some embodiments, administering the gelsolin agent to the subject maintains the status of one or more of: muscle wasting, cachexia, physical injury, impaired locomotion, and decreased physical stability in the subject as compared to the status of each of the characteristics, respectively, prior to the administration of the gelsolin agent. In some embodiments, the frailty condition includes an age-related frailty condition. In some embodiments, the frailty condition is not an age-related frailty condition. In some embodiments, the frailty condition is associated with one or more of: a physical trauma, a physical confinement, a hospitalization, chronic physical inactivity, limited mobility, diabetes, a disease condition, paralysis, and a chronic disease condition. In some embodiments, the gelsolin agent includes a gelsolin molecule, a functional fragment thereof, or a functional derivative of the gelsolin molecule. In some embodiments, the gelsolin molecule is a plasma gelsolin (pGSN). In some embodiments, the gelsolin molecule is a recombinant gelsolin molecule. In some embodiments, a means of administering the gelsolin agent is independently selected from: oral, sublingual, buccal, intranasal, intravenous, intramuscular, intrathecal, intraperitoneal, subcutaneous, intradermal, topical, rectal, vaginal, intrasynovial, and intra-ocular administration. In some embodiments, the subject is one or more of: suspected of having the frailty condition, at risk of having the frailty condition, and diagnosed as having the frailty condition. In some embodiments, the subject is at least 60, 65, 70, 75, 80, 85, 90, 95, or 100 years old. In some embodiments, the subject is between 60 and 70, 60 and 80, 60 and 90, 60 and 100, 70 and 80, 70 and 90, 70 and 100, 80 and 90, 80 and 100, and/or 90 and 100 years old. In some embodiments the subject is between 100 and 110 years old. In some embodiments, the subject is not less than 65, 70, 75, 80, 85, 90, 95, or 100 years old. In some embodiments, the subject is not more than 65 years old. In some embodiments, the subject is between 1 and 65, 5 and 65, 10 and 65, 15 and 65, 20 and 65, 25 and 65, 30 and 65, 35 and 65, 40 and 65, 45 and 65, 50 and 65, 55 and 65, 20 and 40, 30 and 40, 30 and 50, or 60 and 65 years old. In some embodiments, the subject is a mammal. In some embodiments, the subject is a human.

According to an aspect of the invention, a method of selecting a treatment for a subject suspected of having a frailty condition is provided, the method including identifying the presence or absence of one or more of a characteristic of the subject's frailty condition. In some embodiments, the characteristics of the frailty condition includes one or more of: weight loss, exhaustion, weakness, and physical inactivity. In some embodiments, the subject exhibits at least 1, 2, 3, or 4 of the frailty characteristics. In some embodiments, the subject exhibits 1 or 2 of the frailty characteristics, or exhibits 3 or 4 of the frailty characteristics. In some embodiments, the method also includes determining a status of one or more of the characteristics of the frailty condition exhibited by the subject, wherein the status of the one or more characteristics is determined at 1, 2, 3, 4, 5, 6, 7, 8, 9, 10, or more different time points. In some embodiments, the status of the one or more characteristics is determined at one of more of: (1) a time prior to administering a gelsolin agent to the subject; and (2) a time after administering the gelsolin agent to the subject. In some embodiments, the method also includes comparing the determined status of the one or more characteristics in the subject with a control status of the one or more frailty characteristics, respectively, wherein an improvement in the determined status of at least one of the characteristics in the subject compared to the control status of the characteristic, indicates effectiveness of the administered gelsolin in the subject. In some embodiments, the control status includes the status of the characteristic in the subject prior to the administering of the gelsolin agent. In some embodiments, the method also includes selecting a treatment for the subject based at least in part on the identified status of the one or more characteristics. In some embodiments, the method also includes administering the selected treatment to the subject. In some embodiments, the selected treatment includes administration of a gelsolin agent, wherein the gelsolin agent includes a gelsolin molecule, a functional fragment thereof, or a functional derivative of the gelsolin molecule. In some embodiments, the gelsolin molecule is a plasma gelsolin (pGSN). In some embodiments, the gelsolin molecule is a recombinant gelsolin molecule. In some embodiments, the subject is one or more of: suspected of having the frailty condition, at risk of having the frailty condition, and diagnosed as having the frailty condition. In some embodiments, the subject is at least 60, 65, 70, 75, 80, 85, 90, 95, or 100 years old. In some embodiments, the subject is between 60 and 70, 60 and 80, 60 and 90, 60 and 100, 70 and 80, 70 and 90, 70 and 100, 80 and 90, 80 and 100, and/or 90 and 100 years old. In some embodiments the subject is between 100 and 110 years old. In some embodiments, the subject is not less than 65, 70, 75, 80, 85, 90, 95, or 100 years old. In some embodiments, the subject is not more than 65 years old. In some embodiments, the subject is between 1 and 65, 5 and 65, 10 and 65, 15 and 65, 20 and 65, 25 and 65, 30 and 65, 35 and 65, 40 and 65, 45 and 65, 50 and 65, 55 and 65, 20 and 40, 30 and 40, 30 and 50, or 60 and 65 years old. In some embodiments, the subject is a mammal. In some embodiments, the subject is a human. In some embodiments, the frailty condition includes an age-related frailty condition. In some embodiments, the frailty condition is not an age-related frailty condition. In some embodiments, the frailty condition is associated with one or more of: a physical trauma, a physical confinement, a hospitalization, chronic physical inactivity, limited mobility, diabetes, a disease condition, paralysis, and a chronic disease condition. In some embodiments, the selected treatment includes beginning administration of a gelsolin agent to the subject or increasing an amount of a gelsolin agent administered to the subject. In some embodiments, the method also includes treating the subject with the selected treatment.

DETAILED DESCRIPTION

Figure 1:
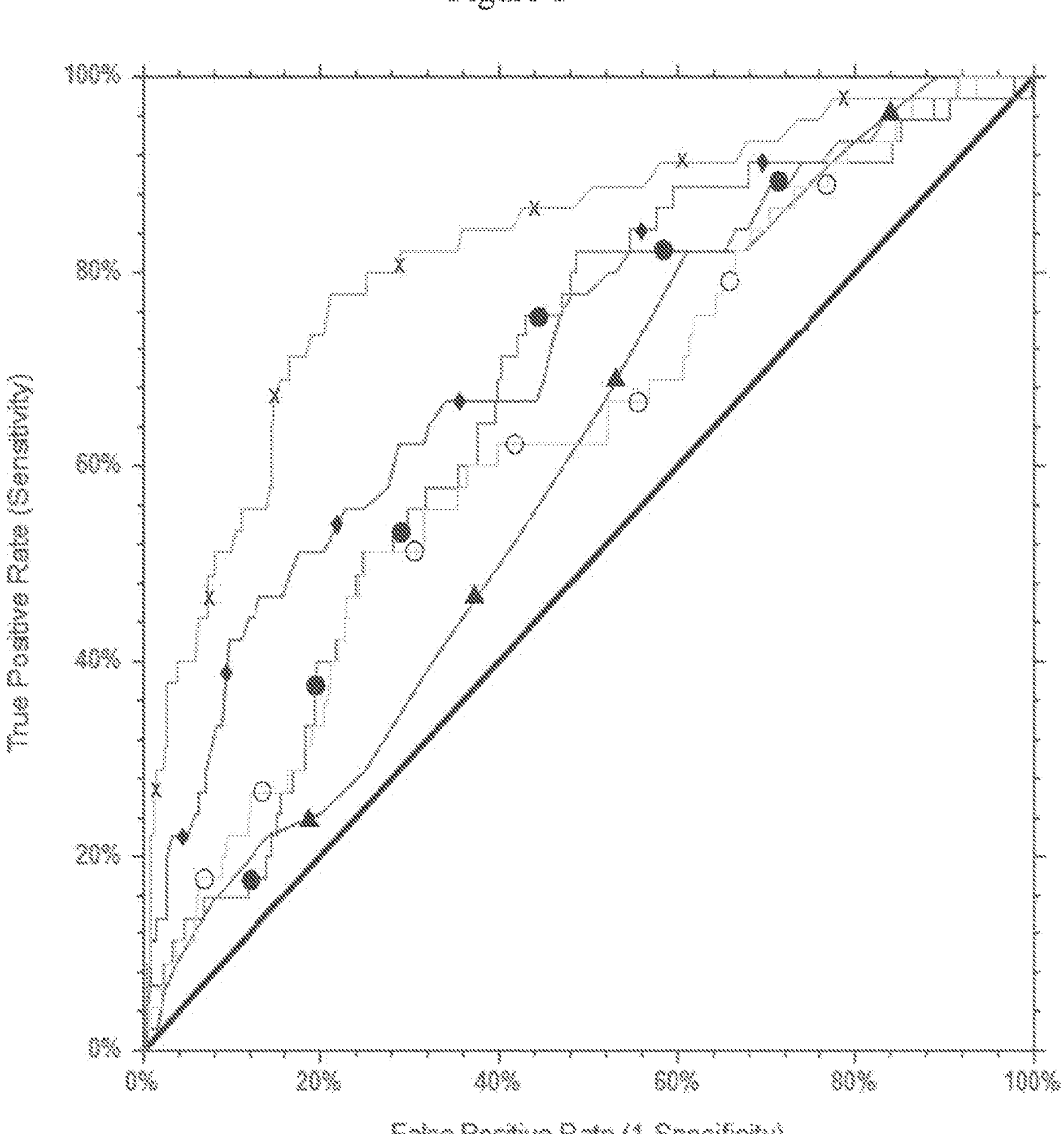
FIG. 1 shows a graph of receiver operating characteristic (ROC) curves between frailty and clinical and laboratory variables. The clinical and laboratory variables shown are selected from those in Table 1 having a significant association with frailty. The line with Xs indicates results for the variable walking speed. The line with diamonds indicates results for the variable peak expiratory flow (PEF). The line with closed circles indicates results for the variable plasma gelsolin. The line with open circles indicates results for the variable LDL cholesterol. The line with triangles indicates results for the variable prealbumin.

The present invention is based, in part, on the discovery that plasma gelsolin (pGSN) levels are reduced in individuals who meet criteria for frailty and that pGSN in subjects is significantly correlated with frailty status and mortality. The term "treatment" or "treating' is intended to include prophylaxis, amelioration, prevention, or cure of the disease.

Frailty and Frailty Conditions

A "frailty condition" is defined herein as physical condition in a subject. A frailty condition comprises a set of frailty characteristics that may be present in the subject. Four frailty characteristics that are used in assessments and methods of the invention are: weight loss, exhaustion, physical weakness, and physical inactivity in a subject. These frailty characteristics may also be herein referred to as "modified phenotypic criteria." In certain embodiments of methods of the invention, frailty in a subject is defined as the subject having, (also referred to herein as "exhibiting") at least 1, 2, 3, or 4 of the frailty characteristics. In certain embodiments of the invention a subject exhibits 1 or 2 of the frailty characteristics and in some embodiments of the invention, a sub has 3 or 4 of the frailty characteristics. Methods of the invention may include determining a status of one or more characteristics of a frailty condition in a subject.

The term "status" as used herein in relation to a characteristic or symptom in a subject, may be the presence, absence, level, severity of the characteristic or symptom in the subject. For example, the status of physical weakness in a subject may be determined to be the presence of a level of weakness in an extremity of the subject. Determining a status of a characteristic of a frailty condition may include one or more means such as physical testing, a questionnaire, visual observation, and other art-known methods. In some embodiments of the invention, a determined status of a characteristic or symptom is compared to a control status of the characteristic or symptom.

Weight loss, exhaustion, physical weakness, and physical inactivity are identified herein as characteristics of a frailty condition, and methods of the invention and the status of one or more of these frailty characteristics may be determined in a subject according to embodiments of methods of the invention. The term "weight loss" as used herein in reference to a frailty characteristic is defined as more than a 2%, 3%, 4%, 5%, 6%, 7%, 8%, 9%, 10%, 11%, 12%, 13%, 14,%, 15%, 16%, 17%, 18%, 19%, or 20% weight loss in a subject compared to a baseline weight for the subject. In some embodiments of the invention, "weight loss" may mean a weight that is significantly lower than a control weight, based on a subjects height, body type, etc. For example, in certain embodiments of methods of the invention, a subject whose weight is or is at least 5%, 6%, 7%, 8%, 9%, 10%, 11%, 12%, 13%, 14,%, 15%, 16%, 17%, 18%, 19%, 20%, 21%, 22%, 23%, 24%, or 25% lower than a control weight may be determined to have a frailty characteristic of weight loss.

Methods of the invention may include determining a status of frailty characteristics of physical weakness and exhaustion in a subject. A status of physical weakness and a status of exhaustion may be determined through one or more of: observation, physical testing, a survey, questionnaire, or other self-reporting tool, for example but not limited to one or more questions from an art-known physical function scale and/or a vitality scale, respectively. Non-limiting examples of such scales are described in: Hays, R. & Morales, L., (2001) Ann Med, 33:350-357; and Sirola J, et al., (2011) J Nutr Health Aging, 15:783-787, the content of each is incorporated by reference in its entirety.

Methods of the invention may include determining a status of physical inactivity in a subject. A status of physical inactivity may be determined through observation, activity monitoring, a survey, questionnaire, physical testing, or other art-known means. In a non-limiting example, determining a status of physical inactivity in a subject is based, in part, on the subject's response to a question such as"do you exercise regularly weekly?" wherein an answer of "no" is taken to denote low physical activity [Sirola J, et al., (2011) J Nutr Health Aging, 15:783-787].

Methods of the invention may include determining whether a subject has a frailty condition. In some embodiments of the invention, a subject is characterized as having a frailty condition, if the subject presents three or four of the frailty characteristics. A subject may be characterized as "prefrail," if the subject presents one to two of the frailty characteristics, or as "non-frail," if the subject does not present any of the four described frailty characteristics, which are recognized in the art as predictive of frailty.

Certain embodiments of methods of the invention may include determining the status of a subject's frailty condition using a frailty index, in which frailty is characterized as an ongoing accumulation of deficits, which are expressed as a list of variables, which may include but are not limited to diseases and other health conditions and activities of daily living (ADLs). Such indices are known in the art, see for example, Searle, S. et al., (2008) Geriatrics, 8:24 and Song, X., et al., (2010) J Am Geriatr Soc., 58(4):681-7, each of which is incorporated by reference herein in its entirety. In some embodiments of the invention, a frailty index for a subject may be calculated by dividing the number of reported variables by the total number of variables, resulting in a score that ranges in value between 0 and 1, with a higher score indicating a more severe status than a lower score.

In some embodiments of the invention, a frailty condition may include an age-related frailty condition, present in a subject at least 60, 65, 70, 75, 80, 85, 90, 95, 100 or more years old. In other embodiments of the invention, a frailty condition may not be an age-related frailty condition. In some embodiments, a non-age-related frailty condition is a frailty condition in a subject less than 70, 65, 60, 55, 50, 45, 40, 35, 30, 25, 20, 15, or 10 years old. In some embodiments of the invention, a frailty condition in a subject is co-morbid with (also referred to herein as "associated with") one of more of a physical trauma, a physical confinement, a hospitalization, chronic physical inactivity, limited mobility, diabetes, a disease condition, paralysis, cancer, and a chronic disease condition. In certain embodiments, a frailty condition in a subject is co-morbid with muscle wasting, sarcopenia, or cachexia. In other embodiments, a subject with a frailty condition does not have cancer.

As used herein, the term "physical trauma" or "physical injury" includes but is not limited to: loss of one or more appendages, one or more broken bones, damage to one or more ligaments, damage to one or more tendons, one or more deep wounds, one or more open wounds, concussion, internal injury, hemorrhage, brain injury, stroke, or surgery. The terms "physical confinement, "hospitalization" are used in reference to a period of inactivity, which in some embodiments take place over an extended period of time. Non-limiting examples of the inpatient medical care and/or treatment delivered for an extended period of time at one or more of a hospital, nursing home, long-term care facility, assisted living facility, hospice, or in a patient's home or residence, and in some embodiments encompasses frequent or recurring confinements and/or hospitalizations. In some embodiments, a confinement or hospitalization lasts, or lasts at least 2, 3, 4, 5, 6, 7, 8, 9, 10, 11, 12, 13, 14, 15, 16, 17, 18, 19, 20, 25, 30, 35, 40, 45, 50, 55, or 60 days. In some embodiments, a period of confinement or hospitalization may last or may last more than 3, 4, 5, 6, 7, 8, 9, 10, 11, or 12 months. In certain embodiments, confinement and/or hospitalization in a subject includes 1, 2, 3, 4, 5, 6, 7, 8, 9, 10 or more instances of confinement and/or hospitalization within the period of 1, 2, 3, 4, or 5 or more years.

As used herein, the term "limited mobility" includes but is not limited to: difficulty in standing up or remaining standing, difficulty sitting down, difficulty walking, and difficulty climbing stairs unaided. The terms "physical stability" or "stability" are used herein in reference to: actions such as, but not limited to: balance when standing, walking, or climbing stairs; or gait when walking and/or climbing stairs. In a non-limiting example, a decrease in a subject physical stability may comprise an increasingly unsteady or uneven gait when walking or climbing stairs. The term "chronic inactivity" as used herein includes but is not limited to sitting for long periods of time and reclining or lying down for extended periods of time beyond normal sleep or rest needs.

As used herein, the term "chronic disease condition" refers to a disease condition that persists or persists at least 1, 2, 3, 4, or more months or develops over time, or a disease condition with long-lasting effects. Chronic disease conditions that may be co-morbid with a frailty condition include but are not limited to: chronic kidney disease (CKD), chronic hepatitis, diabetes mellitus (type 1 diabetes, type 2 diabetes, pre-diabetes, gestational diabetes), cancers, hypertension, cerebrovascular disease, heart failure, ischemic cardiopathy, atrial fibrillation, asthma, chronic obstructive pulmonary disease (COPD), Alzheimer's disease, Cerebral palsy, graft-versus-host disease, stroke, osteoarthritis, rheumatoid arthritis, ulcerative colitis, lupus erythematosus, Crohn's disease, coeliac disease, relapsing polychondritis, Ehlers-Danos syndrome, epilepsy, fibromyalgia, HIV/AIDS, myalgic encephalomyelitis, multiple sclerosis, obesity, and osteoporosis.

As used herein, the terms "muscle wasting" and "myopenia" may be used interchangeably to mean a clinically relevant degree of muscle loss associated with either impaired physical functional capacity and/or increased risk of morbidity or mortality. Muscle wasting and/or myopenia in a subject can be determined using art-known methods, and in some embodiments of the invention, muscle wasting or myopenia represents a loss of at least 5% of muscle mass within 6 to 12 months [see for example, Fearon, K. et al., (2011) J. Cachexia Sarcopenia Muscle, 2:1-3, the content of which is incorporated herein by reference]. As used herein, the term "sarcopenia" means the presence of low skeletal muscle mass and either or both of low muscle strength (for example, but not limited to handgrip strength) or low muscle performance (for example, but not limited to walking speed or muscle power). Sarcopenia may be characterized by a progressive and generalized loss of skeletal muscle mass and function, and may be, but need not be, associated with ageing. As used herein, the term "cachexia" means a greater than 5% weight loss in a subject within the previous 3-12 months, together with the presence of a chronic disease, characteristic symptoms, loss of skeletal muscle with or without loss of fat mass, and biochemical abnormalities. Characteristic symptoms of cachexia include one or more of reduced muscle strength, fatigue, anorexia, and a low fat-free mass index. Means of assessing cachexia are known in the art, see for example: Evans, W J et al., (2008) Clin. Nutr., 27(6):793-9; von Haehling, S. and Anker, (2010) J. Cachexia Sarcopenia Muscle, 1:1-5; Fearon, K. et al., (2011) Lancet Oncol., 12(5):489-95; and Rolland, Y. et al., (2011) Curr. Opin. Nutr. Metab. Care, 14(1):15-21), the content of each of which is incorporated by reference herein.

Subjects

As used herein, a subject may be a vertebrate animal including but not limited to a human, mouse, rat, guinea pig, rabbit, cow, dog, cat, horse, goat, and non-human primate, e.g., a monkey. The term "participant" may be used interchangeably herein with the term "subject". In certain aspects of the invention, a subject may be a domesticated animal, a wild animal, or an agricultural animal. Thus, the invention can be used to treat frailty conditions in human and non-human subjects. For instance, methods and compositions of the invention can be used in veterinary applications as well as in human treatment regimens. In some embodiments of the invention, a subject is a human. In some embodiments of the invention, a subject has a frailty condition and is in need of treatment.

In some embodiments, a subject has a frailty condition. In some embodiments, a subject displays 1, 2, 3, or 4 characteristics of a frailty condition, previously defined herein as weight loss, exhaustion, physical weakness, and physical inactivity. Some methods of assessing characteristics of a frailty condition are tests for physical function measuring height, weight, blood pressure, pulse rate, and peak expiratory flow (PEF), measuring walk speed, measuring hand grip strength with a hand-held dynamometer. Additional non-limiting examples of methods of assessing characteristics of a frailty condition are administering a Mini Mental State Examination (MMSE), and administration of questionnaires or interviews. Other methods of assessing the characteristics of a frailty condition in a subject are known by those of ordinary skill in the art and may be used in conjunction with methods of the invention.

In some embodiments, a subject is at an elevated risk of having a frailty condition because the subject has one or more risk factors for a frailty condition. Risk factors for a frailty condition include but are not limited to: a familial history of a frailty condition, anemia, anorexia (including physiologic anorexia of ageing), endocrine system alteration, underweight or overweight, age, cardiovascular disease, diabetes, arthritis, chronic obstructive pulmonary disease, cognitive impairment/cerebral changes, female gender, low socioeconomic status, race/ethnicity, depression, and activity of daily living disability. Factors that may elevate a subject's risk of having a frailty condition, see for example, Martone, A. M. et al., (2013) Nutrients 5(10), 4126-4133; Espinoza, S. and Fried, L. (2007) Clin. Geriatrics, 15(6): 37-44). A degree of risk of developing a frailty condition depends on the multitude and the severity or the magnitude of the risk factors had by a subject. Some methods of assessing the risk of a frailty condition in a subject include but are not limited to: testing for levels of C-reactive protein, factor VIII, and D-dimer, peripheral blood mononuclear cell (PBMC) proliferation, interleukin-6 (IL-6), iron, insulin-like growth factor I (IGF-I), dehydroepiandrosterone sulfate (DHEAS), body weight, and body mass index (BMI). Other methods of assessing the risk of a frailty condition in a subject include but are not limited to: clinical diagnosis of cardiovascular disease, testing diastolic blood pressure, ultrasound measurement of carotid wall thickness, testing for infarct-like lesions on brain magnetic resonance imaging (MRI), echocardiography measurement for abnormal left ventricular wall motion, and testing for major electrocardiogram abnormalities; prior diagnosis of stroke, diabetes, hypertension, arthritis, cancer, and chronic pulmonary disease. Additional methods of assessing the risk of a frailty condition in a subject are known in the art, and include but are not limited to: reporting of gender, race, ethnicity, education level, income level, and depressive symptoms, see for example: Espinoza, S. and Fried, L. (2007) Clin. Geriatrics, 15(6): 37-44, the content of which is incorporated by reference herein. Other art-known methods of assessing a risk of a frailty condition in a subject can be used in conjunction with methods set forth herein.

In some embodiments of the invention a subject does not have one or more of: multiple sclerosis, non-age-related sarcopenia, chronic renal failure, bacterial sepsis, arthritis, a gram-positive bacterial infection, an acid-fast *bacillus* infection, a spirochete infection, an actinomycete infection, a viral infection, a fungal infection, a parasitic infection, a *Ureaplasma* species infection, a *Mycoplasma* species infection, a *Chlamydia* species infection, a *Pneumocystis* species infection, and a cancer.

Gelsolin Agents

Gelsolin is a highly conserved, multifunctional protein, initially described in the cytosol of macrophages and subsequently identified in many vertebrate cells (Piktel E. et al., Int J Mol Sci 2018; 19:E2516; Silacci P. et al., Cell Mol Life Sci 2004; 61:2614-23.) A unique property of gelsolin is that its gene expresses a splice variant coding for a distinct plasma isoform (pGSN), which is secreted into extracellular fluids and differs from its cytoplasmic counterpart (cGSN) by expressing an additional sequence of 25 amino acids. pGSN normally circulates in mammalian blood at concentrations of 200-300 μg/ml, placing it among the most abundant plasma proteins. The term "gelsolin agent" as used herein means a composition that includes a gelsolin molecule, a functional fragment thereof, or a functional derivative of the gelsolin molecule. In some embodiments of the invention, a gelsolin agent only includes one or more of the gelsolin molecule, a functional fragment thereof, or a functional derivative of the gelsolin molecule. In certain embodiments of the invention a gelsolin agent may include one of more additional components, non-limiting examples of which are detectable labels, carriers, delivery agents, etc. In certain aspects of the invention a gelsolin molecule is a plasma gelsolin (pGSN) and in certain instances, a gelsolin molecule is a cytoplasmic GSN. A gelsolin molecule included in compositions and methods of the invention may be a recombinant gelsolin molecule.

As used herein, the term "gelsolin agent" is a compound that includes an exogenous gelsolin molecule. The term "exogenous" as used herein in reference to a gelsolin molecule means a gelsolin molecule administered to a subject, even if the same gelsolin molecule is naturally present in the subject, which may be referred to as an endogenous gelsolin molecule. A gelsolin agent included in a method or composition of the invention may be a wild-type gelsolin molecule (GenBank accession No.: X04412), isoforms, analogs, variants, fragments or functional derivatives of a gelsolin molecule.

In some embodiments of the invention may include a "gelsolin analog," which as used herein refers to a compound substantially similar in function to either the native gelsolin or to a fragment thereof. Gelsolin analogs include biologically active amino acid sequences substantially similar to the gelsolin sequences and may have substituted, deleted, elongated, replaced, or otherwise modified sequences that possess bioactivity substantially similar to that of gelsolin. For example, an analog of gelsolin is one which does not have the same amino acid sequence as gelsolin but which is sufficiently homologous to gelsolin so as to retain the bioactivity of gelsolin. Bioactivity can be determined, for example, by determining the properties of the gelsolin analog and/or by determining the ability of the gelsolin analog to reduce or prevent the effects of an infection. Gelsolin bioactivity assays known to those of ordinary skill in the art.

Certain embodiments of methods and compositions of the invention include fragments of a gelsolin molecule. The term "fragment" is meant to include any portion of a gelsolin molecule which provides a segment of gelsolin that maintains at least a portion or substantially all of a level of bioactivity of the "parent" gelsolin; the term is meant to include gelsolin fragments made from any source, such as, for example, from naturally-occurring peptide sequences, synthetic or chemically-synthesized peptide sequences, and genetically engineered peptide sequences. The term "parent" as used herein in reference to a gelsolin fragment or derivative molecule means the gelsolin molecule from which the sequence of the fragment or derivative originated.

In certain embodiments of methods and compositions of the invention, a gelsolin fragment is a functional fragment and retains at least some up to all of the function of its parent gelsolin molecule. Methods and compositions of the invention, may in some embodiments include a "variant" of gelsolin. As used herein a gelsolin variant may be a compound substantially similar in structure and bioactivity either to native gelsolin, or to a fragment thereof. In certain aspects of the invention, a gelsolin variant is referred to as a functional variant, and retains at least some up to all of the function of its parent gelsolin molecule.

Gelsolin derivatives are also contemplated for inclusion in embodiments of methods and compositions of the invention. A "functional derivative" of gelsolin is a derivative which possesses a bioactivity that is substantially similar to the bioactivity of gelsolin. By "substantially similar" is meant activity which may be quantitatively different but qualitatively the same. For example, a functional derivative of gelsolin could contain the same amino acid backbone as gelsolin but also contains other modifications such as posttranslational modifications such as, for example, bound phospholipids, or covalently linked carbohydrate, depending on the necessity of such modifications for the performance of a therapeutic method of the invention. As used herein, the term is also meant to include a chemical derivative of gelsolin. Such derivatives may improve gelsolin's solubility, absorption, biological half-life, etc. The derivatives may also decrease the toxicity of gelsolin, or eliminate or attenuate any undesirable side effect of gelsolin, etc. Derivatives and specifically, chemical moieties capable of mediating such effects are disclosed in Remington, The Science and Practice of Pharmacy, 2012, Editor: Allen, Loyd V., Jr, 22$^{nd}$ Edition). Procedures for coupling such moieties to a molecule such as gelsolin are well known in the art. The term "functional derivative" is intended to include the "fragments," "variants," "analogues," or "chemical derivatives" of gelsolin.

Assessments and Controls

A frailty condition in a subject can be detected using art-known methods, including but not limited to: assessing one or more characteristics of the frailty condition. Characteristics of a frailty condition detected in a subject can be compared to control values of the characteristics of the frailty condition. A control value may be a predetermined value, which can take a variety of forms. It can be a single cut-off value, such as a median or mean. It can be established based upon comparative groups, such as in groups of individuals having a frailty condition and groups of individuals who have been administered a treatment for the frailty condition, etc. Another example of comparative groups may be groups of subjects having one or more symptoms of or a diagnosis of the frailty condition and groups of subjects without one or more symptoms of or a diagnosis of the frailty condition. The predetermined value, of course, will depend upon the particular population selected. For example, a population of individuals with the frailty condition that have been administered a gelsolin agent may have a one or more different characteristics of the frailty condition than a population of individuals having the frailty condition that have not been administered the gelsolin agent. Accordingly, the predetermined value selected may take into account the category in which an individual falls. Appropriate categories can be selected with no more than routine experimentation by those of ordinary skill in the art.

Controls can be used in methods of the invention to compare characteristics of different control groups, characteristics of a subject with those of a control group, etc. Comparisons between subjects and controls, one control with another control, etc. may be based on relative differences. For example, though not intended to be limiting, a physiological symptom in a subject treated with a therapeutic method of the invention comprising administering to the subject a gelsolin agent, can be compared to the physiological symptom of a control group that has not been administered the gelsolin agent. The comparison may be expressed in relative terms, for example, if weight loss, or a reduced body mass index (BMI), is a characteristic of a frailty condition, a weight or BMI measurement of a subject treated with a therapeutic method of the invention may be compared to a control weight or BMI measurement. In some embodiments, a suitable control is a subject not treated with a therapeutic method of the invention. A comparison of a treated subject versus a control may include comparing percentage differences in weight or BMI between the treated subject and the selected control. In some instances, a weight or BMI measurement of a subject treated with a method of the invention may be determined to be higher relative to a selected control, with the comparison indicating a, or an at least, 0.1%, 0.5%, 1.0%, 1.5%, 2%, 2.5%, 3%, 3.5%, 4%, 4.5%, 5.0%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, or 20% or higher weight or BMI in the subject as compared to the weight or BMI level in the control. In some certain instances, a weight or BMI measurement of a subject treated with a method of the invention may be determined to be lower relative to a selected control, with the comparison indicating a, or an at least, 0.1%, 0.5%, 1.0%, 1.5%, 2%, 2.5%, 3%, 3.5%, 4%, 4.5%, 5.0%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, or 20% or lower weight or BMI in the subject as compared to the weight or BMI level in the control.

In other embodiments, if physical weakness is a characteristic of a frailty condition, an evaluation of physical strength of a subject treated with a therapeutic method of the invention may be compared to a control evaluation of physical strength. In some embodiments, a suitable control is a subject not treated with a therapeutic method of the invention. A comparison of a treated subject versus a control may include comparing percentage differences in physical strength between the treated subject and the selected control. In some instances, an evaluation of physical strength of a subject treated with a method of the invention may be determined to be lower relative to a selected control, with the comparison indicating a, or an at least, 0.1%, 0.5%, 1.0%, 1.5%, 2%, 2.5%, 3%, 3.5%, 4%, 4.5%, 5.0%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, or 20% or lower level of physical strength of the subject as compared to the level of the control. In some certain instances, an evaluation of physical strength of a subject treated with a method of the invention may be determined to be higher relative to a selected control, with the comparison indicating a, or an at least, 0.1%, 0.5%, 1.0%, 1.5%, 2%, 2.5%, 3%, 3.5%, 4%, 4.5%, 5.0%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, or 20% or higher physical strength of the subject as compared to level of the control.

In some embodiments, if exhaustion is a characteristic of a frailty condition, an evaluation of exhaustion of a subject treated with a therapeutic method of the invention may be compared to a control evaluation of exhaustion. In some embodiments, a suitable control is a subject not treated with a therapeutic method of the invention. A comparison of a treated subject versus a control may include comparing frequency of experiencing exhaustion between the treated subject and the selected control. In some instances, an evaluation of exhaustion of a subject treated with a method of the invention may be determined to be lower relative to a selected control, with the comparison indicating a, or an at least, 0.5%, 1.0%, 2%, 5.0%, 10%, 15%, 20%, 25%, 30%, 35%, 40, 45%, 50%, 55%, 60%, 65%, 70%, 75%, 80%, 85%, 90%, 95%, 100% or lower frequency of exhaustion of the subject as compared to the level of the control. In some certain instances, an evaluation of exhaustion of a subject treated with a method of the invention may be determined to be higher relative to a selected control, with the comparison indicating a, or an at least, 0.5%, 1.0%, 2%, 5.0%, 10%, 15%, 20%, 25%, 30%, 35%, 40, 45%, 50%, 55%, 60%, 65%, 70%, 75%, 80%, 85%, 90%, 95%, 100% or higher frequency of exhaustion of the subject as compared to level of the control.

In other embodiments, if physical inactivity is a characteristic of a frailty condition, an evaluation of physical inactivity of a subject treated with a therapeutic method of the invention may be compared to a control evaluation of physical activity. In some embodiments, a suitable control is a subject not treated with a therapeutic method of the invention. A comparison of a treated subject versus a control may include comparing percentage differences in physical inactivity between the treated subject and the selected control. In some instances, an evaluation of physical inactivity of a subject treated with a method of the invention may be determined to be higher relative to a selected control, with the comparison indicating a, or an at least, 0.5%, 1.0%, 2%, 5.0%, 10%, 15%, 20%, 25%, 30%, 35%, 40, 45%, 50%, 55%, 60%, 65%, 70%, 75%, 80%, 85%, 90%, 95%, 100% or higher level of physical inactivity of the subject as compared to the level of the control. In some certain instances, an evaluation of physical inactivity of a subject treated with a method of the invention may be determined to be lower relative to a selected control, with the comparison indicating a, or an at least, 0.5%, 1.0%, 2%, 5.0%, 10%, 15%, 20%, 25%, 30%, 35%, 40, 45%, 50%, 55%, 60%, 65%, 70%, 75%, 80%, 85%, 90%, 95%, 100% or lower physical inactivity of the subject as compared to level of the control.

In another non-limiting example, a status of a frailty condition and/or a level of plasma gelsolin can be determined using an assay to detect the presence and level of gelsolin in a biological sample that is obtained from a subject having or at risk of having a frailty condition. The results of the assay in a subject treated using a therapeutic method of the invention can be compared to a control level of gelsolin, for example results of the assays on a sample obtained from a control subject not having been so treated. Results of assays to assess a level of gelsolin in a subject treated using a method of the invention can be compared to a control to determine a percentage difference between the subject and the control levels. In some embodiments, a level of a treated subject's gelsolin is greater than 100% of a control level. In certain embodiments of the invention the level of the treated subject's gelsolin is greater than or equal to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1%. 0.9%, 0.8%, 0.7%, 0.6%, 0.5%, 0.4%, 0.3%, 0.2%, or 0.1% of the control level of gelsolin.

In another non-limiting example, a therapeutic effect of a gelsolin agent using a method of the invention can be determined by comparing a likelihood of survival of a subject treated with a method or composition of the invention with a control likelihood of survival. A non-limiting example of a control likelihood of survival is the likelihood of survival in a subject with a frailty condition not treated with a method of the invention. Non-limiting examples of parameters of likelihood of survival that can be measured include: determination of length of time (weeks, months, years etc.) a subject remains alive following a treatment of the invention, and whether a subject dies or survives following a treatment of the invention. It will be understood how these and other parameters relating to likelihood of survival can be compared to controls to assess and determine therapeutic effectiveness of a method or composition of the invention. A non-limiting example of a control of likelihood of survival is the number of years a subject survives after treatment with a method of the invention compared to the control number of years of survival in the absence of the administration of an effective amount of the gelsolin agent. In some embodiments of the invention a likelihood of survival of a subject treated with a synergistic method of the invention is, or is at least, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, 100%, 125%, 150%, 175%, 200%, 300%, 400%, 500%, higher than a control likelihood of survival.

It will be understood that controls may be, in addition to predetermined values, biological samples tested in parallel with experimental (physical, physiological, and question-based) measurements. Examples include samples from control populations or control samples generated through manufacture to be tested in parallel with the experimental samples; and also a control may be a sample from a subject prior to, during, or after a treatment with an embodiment of a method or composition of the invention. Thus one or more characteristics determined for a subject having a frailty condition may be used as "control" values for those characteristics in that subject at a later time.

In some embodiments of the invention effectiveness of a method of the invention can be assessed by comparing therapeutic results in a subject treated using a method of the invention to an individual therapeutic effect of the gelsolin agent. In certain aspects of the invention, a difference in a level of therapeutic effectiveness may be assessed on a scale indicating an increase from a control level. In some aspects an increase is from a control level of zero obtained in (1) or (2) to a level greater than zero resulting from treatment with a method of the invention. In some embodiments of the invention, a level of therapeutic effect of a therapeutic method of the invention is an increase of, or at least, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, 100%, 125%, 150%, 175%, 200%, 300%, 400%, 500%, or more from a control level of therapeutic effect.

Preparation and Administration of Pharmacological Agents

Methods and compositions of the invention have important implications for patient treatment and also for the clinical development of new therapies. It is also expected that aspects of the invention can be used by clinical investigators to determine entry criteria for human subjects in clinical trials. Health care practitioners select therapeutic regimens for treatment based upon the expected net benefit to the subject. The net benefit is derived from the risk to benefit ratio.

The amount of a treatment may be varied for example by increasing or decreasing the amount of gelsolin agent administered to a subject, by changing the therapeutic composition administered, by changing the route of administration, by changing the dosage timing and so on. The effective amount will vary with the particular condition being treated, the age and physical condition of the subject being treated, the severity of the infection or condition, the duration of the treatment, the specific route of administration, and like factors are within the knowledge and expertise of the health practitioner. For example, an effective amount can depend upon how long or the degree to which an individual has been affected by the frailty condition.

Effective Amounts

The term "effective amount" as used herein relates to a treatment method or composition of the invention. Methods of the invention comprise administering a gelsolin agent in an amount that is an effective amount. When administered to a subject in a method of the invention, an effective amount of the gelsolin agent results in a therapeutic effect against and/or a reduction in the frailty condition in the subject.

An effective amount is a dosage of a pharmacological agent sufficient to provide a medically desirable result. Examples of pharmacological agents that may be used in certain embodiments of compositions and methods of the invention include, but are not limited to gelsolin agents. It should be understood that pharmacological agents of the invention are used to treat or prevent frailty conditions, that is, they may be used prophylactically in subjects at risk of developing a frailty condition. Thus, an effective amount is that amount which can lower the risk of, slow, or perhaps prevent altogether the development of a frailty condition. It will be recognized when the pharmacologic agent is used in acute circumstances, it is used to prevent one or more medically undesirable results that typically flow from such adverse events.

Factors involved in determining an effective amount are well known to those of ordinary skill in the art and can be addressed with no more than routine experimentation, including but not limited to clinical trials to assess dosage. It is generally preferred that a maximum dose of the pharmacological agents of the invention (alone or in combination with other therapeutic agents) be used, that is, the highest safe dose according to sound medical judgment. It will be understood by those of ordinary skill in the art however, that a patient may insist upon a lower dose or tolerable dose for medical reasons, psychological reasons, or for virtually any other reasons.

The therapeutically effective amount of a pharmacological agent of the invention is that amount effective to treat the disorder, such as a frailty condition. In the case of a frailty condition the desired response is inhibiting the progression of and/or reducing the severity of the frailty condition. This may involve only slowing the progression of the frailty condition temporarily, although it may include halting the progression of the frailty condition permanently. Inhibiting the progression of and/or reducing the severity of a frailty condition may also involve reducing the severity of the one or more characteristics of the frailty condition in a subject by, or by at least 1%, 2%, 5%, 10%, 15%, 20%, 25%, 30%, 35%, 40%, 45%, 50%, 55%, 60%, 65%, 70%, 75%, 80%, 85%, 90%, 95%, or more as compared to a baseline level of severity of the one or more characteristics of the frailty condition in the subject. This may also include reducing the number of frailty condition characteristics exhibited by a subject from 4 to 3 or from 3 to 2 or from 2 to 1 or from 1 to 0 compared to a baseline number of frailty condition characteristics observed in the subject. This can be monitored by routine diagnostic methods known to those of ordinary skill in the art. The desired response to treatment of the frailty condition also can be delaying the onset of or even preventing the onset of the frailty condition.

Pharmaceutical Agents and Delivery

The pharmacological agents used in the methods of the invention are preferably sterile and contain an effective amount of gelsolin agent for producing the desired response in a unit of weight or volume suitable for administration to a subject. Doses of pharmacological agents administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits. The dosage of a pharmacological agent may be adjusted by the individual physician or veterinarian, particularly in the event of any complication. A therapeutically effective amount typically varies from 0.01 mg/kg to about 1000 mg/kg, from about 0.1 mg/kg to about 200 mg/kg, from about 0.2 mg/kg to about 20 mg/kg, from about 0.5 mg/kg to about 10 mg/kg, or from about 1.0 mg/kg to about 5 mg/kg in one or more dose administrations daily, for one or more days. In some embodiments of the invention, a therapeutically effect amount varies from 1 mg/kg to 100 mg. Gelsolin agents may also be referred to herein as pharmacological agents.

Various modes of administration are known to those of ordinary skill in the art which effectively deliver the pharmacological agents of the invention to a desired tissue, cell, or bodily fluid. The manner and dosage administered may be adjusted by the individual physician, healthcare practitioner, or veterinarian, particularly in the event of any complication. The absolute amount administered will depend upon a variety of factors, including the material selected for administration, whether the administration is in single or multiple doses, and individual subject parameters including age, physical condition, size, weight, and the stage of the disease or condition. These factors are well known to those of ordinary skill in the art and can be addressed with no more than routine experimentation.

Pharmaceutically acceptable carriers include diluents, fillers, salts, buffers, stabilizers, solubilizers and other materials that are well-known in the art. Exemplary pharmaceutically acceptable carriers are described in U.S. Pat. No. 5,211,657 and others are known by those skilled in the art. In certain embodiments of the invention, such preparations may contain salt, buffering agents, preservatives, compatible carriers, aqueous solutions, water, etc. When used in medicine, the salts may be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

Various modes of administration known to the skilled artisan can be used to effectively deliver pharmaceutical composition of the invention that comprises a gelsolin agent to a subject to produce a therapeutic effect in the subject. Methods for administering such a composition or pharmaceutical compound of the invention may be topical, intravenous, oral, intracavity, intrathecal, intrasynovial, buccal, sublingual, intranasal, transdermal, intravitreal, subcutaneous, intramuscular, and/or intradermal administration. The invention is not limited by the particular modes of administration disclosed herein. Standard references in the art (e.g., Remington, The Science and Practice of Pharmacy, 2012, Editor: Allen, Loyd V., Jr, 22$^{nd}$ Edition) provide modes of administration and formulations for delivery of various pharmaceutical preparations and formulations in pharmaceutical carriers. Other protocols which are useful for the administration of a therapeutic compound of the invention will be known to a skilled artisan, in which the dose amount, schedule of administration, sites of administration, mode of administration (e.g., intra-organ) and the like vary from those presented herein. Other protocols which are useful for the administration of pharmacological agents of the invention will be known to one of ordinary skill in the art, in which the dose amount, schedule of administration, sites of administration, mode of administration and the like vary from those presented herein.

Administration of pharmacological agents of the invention to mammals other than humans, e.g. for testing purposes or veterinary therapeutic purposes, is carried out under substantially the same conditions as described above. It will be understood by one of ordinary skill in the art that this invention is applicable to both human and animal diseases. Thus, this invention is intended to be used in husbandry and veterinary medicine as well as in human therapeutics. A pharmacological agent may be administered to a subject in a pharmaceutical preparation.

When administered, the pharmaceutical preparations of the invention are applied in pharmaceutically-acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

A pharmacological agent or composition may be combined, if desired, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the pharmacological agents of the invention, and with each other, in a manner such that there is no interaction which would substantially impair the desired pharmaceutical efficacy.

The pharmaceutical compositions may contain suitable buffering agents, as described above, including: acetate, phosphate, citrate, glycine, borate, carbonate, bicarbonate, hydroxide (and other bases) and pharmaceutically acceptable salts of the foregoing compounds. The pharmaceutical compositions also may contain, optionally, suitable preservatives, such as: benzalkonium chloride; chlorobutanol; parabens and thimerosal.

The pharmaceutical compositions may conveniently be presented in unit dosage form and may be prepared by any of the methods well known in the art of pharmacy. All methods include the step of bringing the active agent into association with a carrier, which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, pills, lozenges, each containing a predetermined amount of the active compound (e.g., gelsolin). Other compositions include suspensions in aqueous liquids or non-aqueous liquids such as a syrup, elixir, an emulsion, or a gel.

Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, i.e. EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Adducts" In: Enzymes as Drugs, Hocenberg and Roberts, eds., Wiley-Interscience, New York, N.Y., pp. 367-383; Newmark, et al., 1982, J. Appl. Biochem. 4:185-189. Other polymers that could be used are poly-1,3-dioxolane and poly-1,3,6-tioxocane.

For the pharmacological agent the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the gelsolin agent or by release of the biologically active material beyond the stomach environment, such as in the intestine.

Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Also contemplated herein is pulmonary delivery of gelsolin. Gelsolin is delivered to the lungs of a mammal while inhaling and traverses across the lung epithelial lining to the blood stream.

Nasal (or intranasal) delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active compounds may be in powder form for constitution with a suitable vehicle, e.g., sterile pyrogen-free water, before use.

Pharmacological agent(s), including specifically but not limited to a gelsolin agent, may be provided in particles. Particles as used herein means nano or microparticles (or in some instances larger) which can consist in whole or in part of the gelsolin agent as described herein. The particles may contain the pharmacological agent(s) in a core surrounded by a coating, including, but not limited to, an enteric coating. The pharmacological agent(s) also may be dispersed throughout the particles. The pharmacological agent(s) also may be adsorbed into the particles. The particles may be of any order release kinetics, including zero order release, first order release, second order release, delayed release, sustained release, immediate release, and any combination thereof, etc. The particle may include, in addition to the pharmacological agent(s), any of those materials routinely used in the art of pharmacy and medicine, including, but not limited to, erodible, nonerodible, biodegradable, or nonbiodegradable material or combinations thereof. The particles may be microcapsules which contain the gelsolin in a solution or in a semi-solid state. The particles may be of virtually any shape.

Both non-biodegradable and biodegradable polymeric materials can be used in the manufacture of particles for delivering the pharmacological agent(s). Such polymers may be natural or synthetic polymers. The polymer is selected based on the period of time over which release is desired. Bioadhesive polymers of particular interest include bioerodible hydrogels described by H. S. Sawhney, C. P. Pathak and J. A. Hubell in Macromolecules, (1993) 26:581-587, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly (octadecyl acrylate).

The pharmacological agent(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug therefrom. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the pharmacological agent(s) for at least 7 days, and preferably 30-60 days. Long-term sustained release implants are well-known to those of ordinary skill in the art and include some of the release systems described above.

The invention also contemplates the use of kits. In some aspects of the invention, the kit can include one or more pharmaceutical preparation vials, a pharmaceutical preparation diluent vial, and a gelsolin agent. A vial containing the diluent for the pharmaceutical preparation is optional. A diluent vial may contain a diluent such as physiological saline for diluting what could be a concentrated solution or lyophilized powder of the gelsolin agent. The instructions can include instructions for mixing a particular amount of the diluent with a particular amount of the concentrated pharmaceutical preparation, whereby a final formulation for injection or infusion is prepared. The instructions may include instructions for treating a subject with effective amounts of the gelsolin agent. It also will be understood that the containers containing the preparations, whether the container is a bottle, a vial with a septum, an ampoule with a septum, an infusion bag, and the like, can contain indicia such as conventional markings that change color when the preparation has been autoclaved or otherwise sterilized.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

The following examples are provided to illustrate specific instances of the practice of the present invention and are not intended to limit the scope of the invention. As will be apparent to one of ordinary skill in the art, the present invention will find application in a variety of compositions and methods.

EXAMPLES

Example 1

Methods

Participants

The Helsinki Businessmen Study (HBS) cohort has been described in detail previously: 3,490 men, mostly business executives born between 1919 and 1934, participated in volunteer health check-ups during the 1960s and early 1970s organized by the Finnish Institute of Occupational Health (Strandberg et al., (2016) International J. of Epidemiology Vol. 45, Issue 4 pp. 1074-1074h, doi.org/10.1093/ije/dyv310; Sirola J, et al. (2011) J Nutr Health Aging. 15:783-787). The cohort has been followed up using national registries, regular mailed questionnaire surveys with good response rates, and clinical examinations in random sub-cohorts. The follow-up study described herein was approved by the ethical committee of the Department of Medicine, Helsinki University Central Hospital. The study was registered as ClinicalTrials.gov identifier NCT02526082. The present analysis involved 498 home-dwelling men who were investigated with questionnaires and clinical examinations including laboratory tests in 2010-2011, and subsequent 5-year mortality follow-up through Aug. 31, 2016.

Clinical and Laboratory Investigations After the mailed survey in 2010, a random sample of responders was studied in the clinic; completing the investigation with a venous blood sample for laboratory analyses. Because the time between mailed questionnaire and clinical examination varied, contemporary lifestyle, mental, and functional data were updated through an interview by the study nurse. The questionnaire also included items about self-rated health (RAND-36 wording), instrumental activities of daily life (ADL) functions (help needed, yes/no, in 14 items), and six questions about attitudes towards life.

The clinical investigations included measuring height, weight, blood pressure, pulse rate, tests for physical function (peak expiratory flow [PEF], walk speed, handgrip with a handheld dynamometer), and Mini Mental State Examination (MMSE)). Standard clinical instruments were used and laboratory tests were taken from plasma after a 12-hour fast and included lipids, glucose, insulin, creatinine, high-sensitivity C-reactive protein, alanine aminotransferase (ALT) and prealbumin. The analyses were performed with standard art-known methods at the clinical laboratory of the Oulu University Hospital, Finland. Plasma was also frozen for subsequent laboratory analyses. Studies included detection and assessment of levels of plasma lipids (cholesterol, HDL cholesterol, LDL cholesterol, triglycerides), plasma glucose, plasma insulin, prealbumin, hs C-reactive protein (hsCRP), creatinine, alanine aminotransferase (ALT), homocysteine, and peak expiratory flow (PEF) in the subjects using standard clinical laboratory procedures.

Frailty Assessment

Frailty and pre-frailty were earlier defined in the Helsinki Businessmen Study (FIBS) cohort (in 2000, n=1415) according to modified phenotypic criteria: weight loss, physical weakness, exhaustion, and physical inactivity (Sirola J, et al., (2011) J Nutr Health Aging; 15:783-787). A participant was classified to be frail if 3-4 of the criteria were reported, pre-frail if 1-2 criteria were reported, and not-frail if zero criteria were present. Because this modified definition of frailty has been validated in the HBS cohort and shown to predict important clinical endpoints including walking speed, mobility-disability, and mortality (Sirola J, et al., (2011) J Nutr Health Aging; 15:783-787), this definition was also used in the analysis of the study now described. In addition to phenotypic frailty, a frailty index was calculated in 473 men from 21 self-reported but physician-diagnosed diseases and conditions in the mailed questionnaire (memory disorder, stroke, hypertension, coronary artery disease, heart failure, myocardial infarction, bronchial asthma, chronic obstructive pulmonary disease, peripheral artery disease, diabetes, cancer, rheumatoid arthritis, osteoarthritis, other joint disease, other musculoskeletal disorder, mild psychiatric disorder, serious psychiatric disorder, ulcus disease, prostatic disease, chronic posttraumatic disability, other chronic illness or trauma). Information relating to frailty index calculations can be found in references such as: Searle, S. D. et al., BMC Geriatr. 2008 Sep. 30; 8:24. doi: 10.1186/1471-2318-8-24.

Robust, prefrail, and frail phenotypes were defined according to the following modified phenotypic criteria: (1) shrinking: weight loss (>5% from 2000, or current BMI <18.5 kg/m$^2$); (2) weakness: hand grip strength (cut-off point 27 kg) [Ha Y. C. et al., Eur Geriatr Med. 9, 277-288 (2018)]; (3) exhaustion (reported low energy most or all of the time during the preceding four weeks; one of the questions of the Vitality domain of RAND-36); (4) low activity (based on the question: "Do you exercise regularly weekly?"; a "no" response was taken to denote low physical activity); and (5) slowness (walk speed <0.8 m/s) [Studenski S. et al., JAMA 305(1), 50-58 (2011)].

Mortality

Total mortality of the study cohort through Jul. 31, 2016, was retrieved from the Population Information System, which keeps a registry of all Finnish citizens.

Gelsolin Analysis

Levels of plasma gelsolin (pGSN) in blood samples were determined using an ELISA-based assay to measure gelsolin levels in the plasma of patients. In the assay, a rabbit polyclonal antibody to human plasma gelsolin was utilized as a capture agent for gelsolin in plasma or recombinant gelsolin standard. The bound gelsolin was then detected using a commercially available anti-gelsolin antibody (Sigma clone 2C4) and with HRP conjugated anti-mouse IgG. After each incubation, the ELISA plate was washed to remove the unbound material. The amount of bound HRP conjugated anti-mouse IgG antibody was detected by addition of TMB color reagent. The optical density of the resulted color was directly proportional to the amount of gelsolin in the initial sample and was determined using a standard curve constructed with a recombinant gelsolin reference standard, as well as a plasma standard with a known amount of endogenous plasma gelsolin.

The following protocol was used to measure levels of pGSN in subject plasma samples.

Procedure:

Solutions/Buffers

The following solutions were prepared and used in determinations of pGSN levels in subject plasma samples.

Wash Buffer:

200 ml 10×TBS 4 ml 1M $CaCl_2$ 1 ml Tween 20

Blocking Buffer:

1.5 g Fatty acid free BSA and 50 ml Wash buffer.

Assay Buffer:

50 ml blocking buffer was diluted with 100 ml wash buffer to make a 1% BSA solution.

Dilute GaM-HRP (a 10× Dilution)

8 μl assay buffer

2 μl GaM-HRP

Detection BUFFER

| 15 ml assay buffer | |
|---|---|
| 2 μl GS-2C4 | 7500X |
| 9.38 μl Dilute GαM-HRP | 16000X (total) |

3,3'5,5'-tetramethylbenzidine (TMB) and TMB Stop Solution

Prepared according to manufacturer's instructions.

Assay Procedure

The following procedure was used to determine pGSN levels in subject plasma samples.

(1) Assay plates were coated at 5 μg/ml PoShun AB in carbonate bicarbonate buffer (pH 9.6) at 100 μl/well. The assay plates were sealed and incubated overnight at 4° C.

(2) If more than one plate was run, the plates were staggered at 1 hr intervals. For each assay, the assay plate was brought to room temperature and the plasma samples for that plate thawed.

(3) The assay plate was washed twice with 300 μl/well wash buffer. 250 μl blocking buffer was added to each assay plate well and the plate sealed and incubated 2 hrs at room temperature.

(4) Three dilution plates were labeled: 1, 2, and 3. In plate 1, 140 μl assay buffer was added to columns 4-12. In plate 2, 90 μl assay buffer was added to columns 4-12. In plate 3, 150 μl assay buffer was added to columns 1-3 and 90 μl assay buffer was added to columns 4-12.

(5) The rhuGSN was diluted as follows:

1) 74.8 μl assay buffer
   2 μl rhuGSN 38.4 mg/ml stock
2) 490 μl assay buffer
   10 μl dilution #1
3) 485 μl assay buffer
   15 μl dilution #2

(6) 10 μl plasma from each sample was added to three wells in dilution plate #1 according to plate map.

| | Columns 4, 5, and 6 | Columns 7, 8, and 9 | Columns 10, 11, and 12 |
|---|---|---|---|
| A | Sample #1 | Sample #9 | Sample #17 |
| B | Sample #2 | Sample #10 | Sample #18 |
| C | Sample #3 | Sample #11 | Sample #19 |
| D | Sample #4 | Sample #12 | Sample #20 |
| E | Sample #5 | Sample #13 | Sample #21 |
| F | Sample #6 | Sample #14 | Sample #22 |

-continued

| | Columns 4, 5, and 6 | Columns 7, 8, and 9 | Columns 10, 11, and 12 |
|---|---|---|---|
| G | Sample #7 | Sample #15 | Sample #23 |
| H | Sample #8 | Sample #16 | IR Pooled Plasma Standard |

(7) The contents of the wells were pipetted to mix and 10 μl was transferred from dilution plate #1 to dilution plate #2.

The content of the wells were pipetted to mix and 10 μl from dilution plate #2 was transferred to dilution plate #3. 150 μl of rhuGSN dilution 3 was added to wells A1, A2, A3 and pipetted to mix. A 2× serial dilution of standard down columns 1-3 was performed, stopping at row G (H is background control).

(8) The assay plate was washed wash buffer one time using 300 μl/well wash buffer.

(9) 50 μl detection buffer was added to each well of the assay plate. The dilution plate wells were mixed well by pipetting 50 μl was transferred to each assay plate well. The plate was sealed with adhesive plate seal and incubated 1 h @ room temperature (RT) with shaking.

(10) A 12 ml aliquot of 3,3'5,5'-tetramethylbenzidine (TMB) was prepared using, brought to room temperature while protected from light. The assay plate was washed four times with 300 μl/well wash buffer. After washing 100 μl/well TMB was added and the plate incubated 10 minutes and the reaction stopped by adding 100 μl TMB Stop solution.

(11) The plates were read at @ A450/A650.

Statistical Analyses

Statistical analyses were performed with NCSS 2008 software (NCSS, Kaysville, Utah). Continuous variables are shown as means with SDs, SEs, or medians with interquartile ranges. In addition, Spearman rank correlation and analysis of covariance (ANCOVA) were used to compare groups. Logistic regression was used to identify independent determinants of frailty and prefrailty. The focus was on plasma gelsolin, and clinically meaningful variables which in univariate analyses were related to frailty were selected as covariates. Gelsolin was studied both as a continuous variable and as divided in quartiles (lowest quartile as reference). The results are presented as odds ratios (OR) with their 95% confidence intervals (CI).

Predictors of 5-year mortality were analysed using Cox proportional hazards models; hazards assumptions were tested and met, and results are presented as hazard ratios (HR) with their 95% CIs. Receiver operating characteristic (ROC) curves were used to demonstrate the sensitivity and specificity. P values of less than 0.05 (two-sided) were considered to indicate statistical significance.

Results

Baseline characteristics of the study cohort are shown in Table 1. Median age was 82 years (IQ range 80-85) and range 77-92 years. According to the phenotypic definition, 11.3% (n=56) of the men were defined frail and 51.3% (n=255) as pre-frail. Median frailty index was 0.14 (IQ range 0.10-0.24). Median plasma gelsolin was 57.9 (IQ range 52.3-64.0), and there was a highly significant trend (P=0.0002) between gelsolin and frailty status, whereas gelsolin was not correlated with frailty index (r=−0.02, P=0.67).

Results demonstrated that phenotypic frailty was associated with slower gait speed, weaker grip strength, lower PEF values, and higher frailty index, but of the other clinical and laboratory variables only prealbumin, total and LDL cholesterol were significantly—but more weakly than gelsolin—associated with frailty.

There was also a highly significant (P=0.008) graded association between gelsolin quartiles and frailty status: prevalence of frailty decreased from the lowest to the highest quartile (18.5%, 13.6%, 8.0%, and 4.9%, respectively). The situation was different for 5-year mortality (139 deaths, 28.0%): it was highest in the lowest gelsolin quartile (36.3%) and similar in higher quartiles (24.8%, 24.0% and 26.8%, respectively).

The relationship between gelsolin quartiles and frailty was tested further. In the fully adjusted model and with the lowest quartile (<52.3) as referent there was a graded association with ORs (95% CI) 0.59 (0.24-1.48), 0.29 (0.09-0.91), and 0.17 (0.05-0.62), in the second, third and fourth quartile, respectively. No significant associations were observed between gelsolin quartiles and prefrailty. ROC curves of plasma gelsolin and several other variables to demonstrate discriminating power of frailty status are shown in FIG. 1.

TABLE 1

Age-adjusted characteristics according to frailty at baseline in 2011

| Variable* | All, n = 497 | Not frail n = 186 | Prefrail n = 255 | Frail, n = 56 | p-value for linear trend between frailty groups |
|---|---|---|---|---|---|
| Age, yr | 83.3 (0.2)<br>82 (80-85) | 81.5 (0.2)<br>81 (79-83) | 83.2 (0.2)<br>83 (81-86) | 85.2 (0.5)<br>85 (83-88) | 0.00001 |
| BMI, kg/m$^2$ | 25.1 (0.2) | 25.5 (0.2) | 24.6 (0.2) | 25.1 (0.4) | 0.45 |
| Waist circumference, cm | 98.4 (2.6) | 96.0 (2.9) | 100.4 (2.5) | 98.6 (5.3) | 0.66 |
| Frailty index | 0.17 (0.008) | 0.15 (0.007) | 0.17 (0.006) | 0.22 (0.01 | 0.00009 |
| Plasma gelsolin, µg/mL | 57.0 (0.6) | 59.3 (0.7)<br>58.9 (53.2-64.0) | 58.4 (0.6)<br>57.9 (52.3-64.7) | 53.2 (1.2)<br>53.0 (49.4-58.3) | 0.0002 |
| Plasma lipids, mmol/L | | | | | |
| cholesterol | 4.7 (0.07) | 4.9 (0.08) | 4.8 (0.06) | 4.5 (0.1) | 0.042 |
| HDL cholesterol | 1.5 (0.03) | 1.5 (0.03) | 1.5 (0.03) | 1.5 (0.06) | 0.84 |
| LDL cholesterol | 2.6 (0.05) | 2.8 (0.06) | 2.7 (0.05) | 2.4 (0.1) | 0.003 |
| triglycerides | 1.26 (0.04) | 1.29 (0.05) | 1.28 (0.04) | 1.20 (0.09) | 0.69 |
| Plasma glucose, mmol/L | 5.8 (0.09) | 5.6 (0.1) | 6.0 (0.09) | 5.7 (0.2) | 0.62 |
| Plasma insulin | 14.0 (0.9) | 12.8 (1.1) | 15.3 (0.9) | 13.9 (2.0) | 0.62 |
| Prealbumin | 0.25 (0.003) | 0.26 (0.003) | 0.25 (0.003) | 0.24 (0.006) | 0.014 |
| hs C-reactive protein | 2.6 (0.4) | 1.9 (0.5) | 3.4 (0.4) | 2.4 (0.8) | 0.56 |
| Creatinine | 98.9 (2.0) | 95.6 (2.3) | 98.4 (2.0) | 102.6 (4.2) | 0.14 |
| ALT | 18.5 (0.5) | 19.8 (0.6) | 18.2(0.5) | 17.6 (1.1) | 0.07 |
| Homocysteine | 16.0 | 15.4 (0.4) | 16.1 (0.3) | 16.6 (0.7) | 0.10 |
| PEF | 428.2 (6.0) | 464.5 (6.5) | 434.3 (5.6) | 385.8 (12.7) | 0.0001 |
| Walk speed, m/s | 0.82 (0.01) | 0.96 (0.01) | 0.82 (0.01) | 0.67 (0.02) | 0.0001 |
| Grip strength | 34.9 | 40.3 (0.7) | 36.5 (0.6) | 27.8 (1.3) | 0.0001 |
| 5-year mortality, n (%) | 139 (28.0) | 24 (12.9) | 79 (31.0) | 36 (64.3) | 0.0001 |

BMI = body mass index.
*Age-adjusted, continuous variables are mean (SE).
Log-transformed values where used where indicated.

Independent association of plasma gelsolin with frailty status was tested with logistic regression (Table 2). With prefrailty status as referent, lower gelsolin level was significantly associated with frailty, and this association was insensitive to covariates closely related to frailty. Even with frailty index in the equation, OR of frailty was 47% lower per SD of plasma gelsolin (P=0.003). No significant relationship was observed between gelsolin and prefrailty in these analyses.

TABLE 2

Multivariate-adjusted odds ratios of prefrailty, and frailty in old age according to plasma gelsolin

| | Odds Ratio (OR) 95% Confidence Interval (CI) | | |
|---|---|---|---|
| Gelsolin per SD | Not frail, n = 186 | Prefrail n = 255 | Frail n = 56 |
| Unadjusted | 1.06 (0.87-1.28) | 1.0 (referent) | 0.56 (0.42-0.79) |
| Adjusted for age | 1.10 (0.90-1.33) | 1.0 (referent) | 0.53 (0.38-0.74) |
| Adjusted for age, LDL cholesterol, and prealbumin | 1.06 (0.87-1.30) | 1.0 (referent) | 0.56 (0.40-0.78) |
| Above plus PEF and walk speed | 0.98 (0.78-1.23) | 1.0 (referent) | 0.57 (0.39-0.85) |
| Above plus frailty index | 1.00 (0.79-1.27) | 1.0 (referent) | 0.53 (0.35-0.81) |

Figure 2:
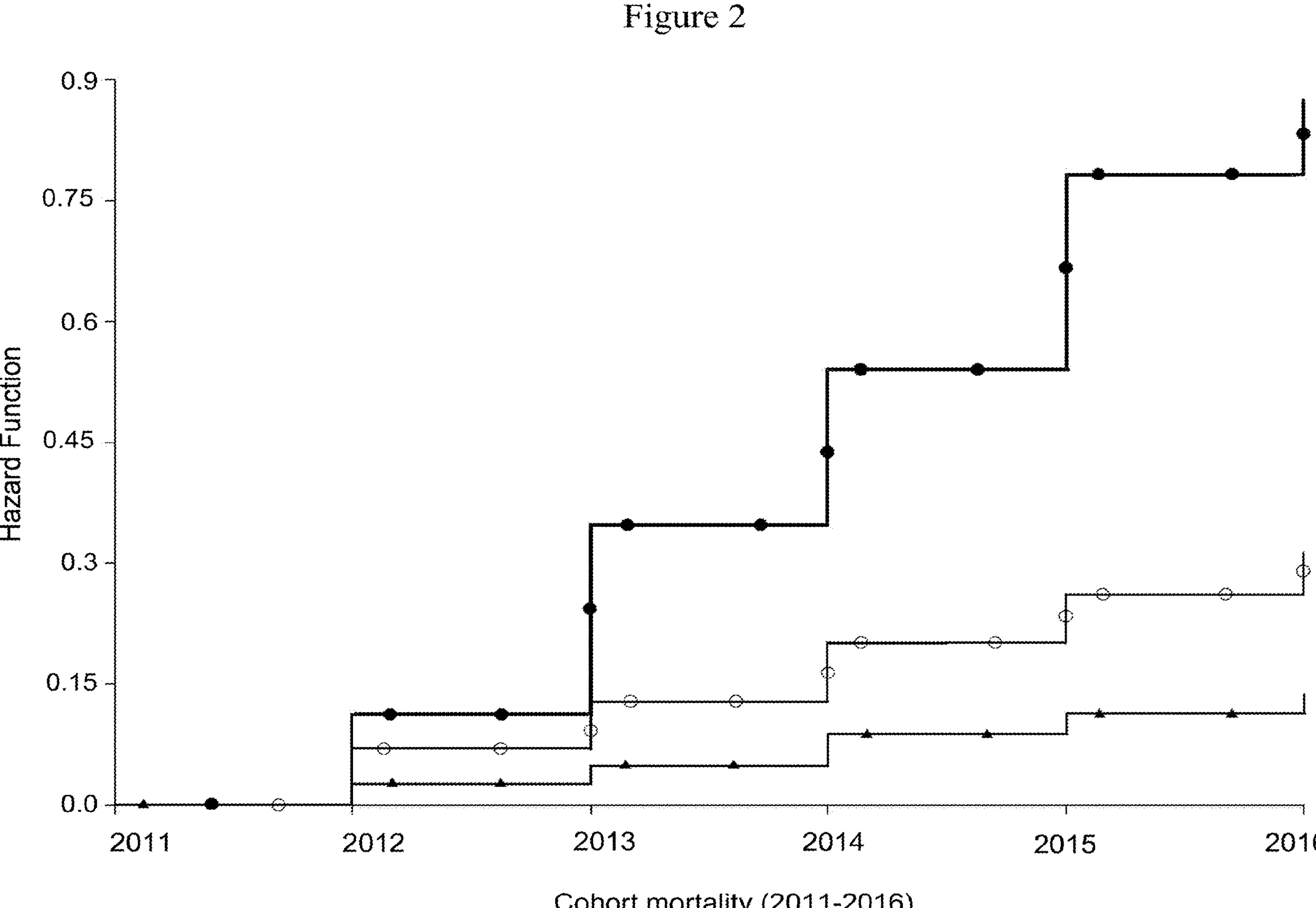
FIG. 2 presents a graph showing five-year mortality of the study cohort according to the baseline frailty status at the beginning of the study. The line with closed circles indicates results from the frail portion of the study cohort. The line with open circles indicates results from the pre-frail portion of the study cohort. The line with triangles indicates results from the non-frail portion of the study cohort. By the second year of the study, the frail proportion showed higher mortality than either of the other categories and continued to do so for the duration of the study.
Figure 3:
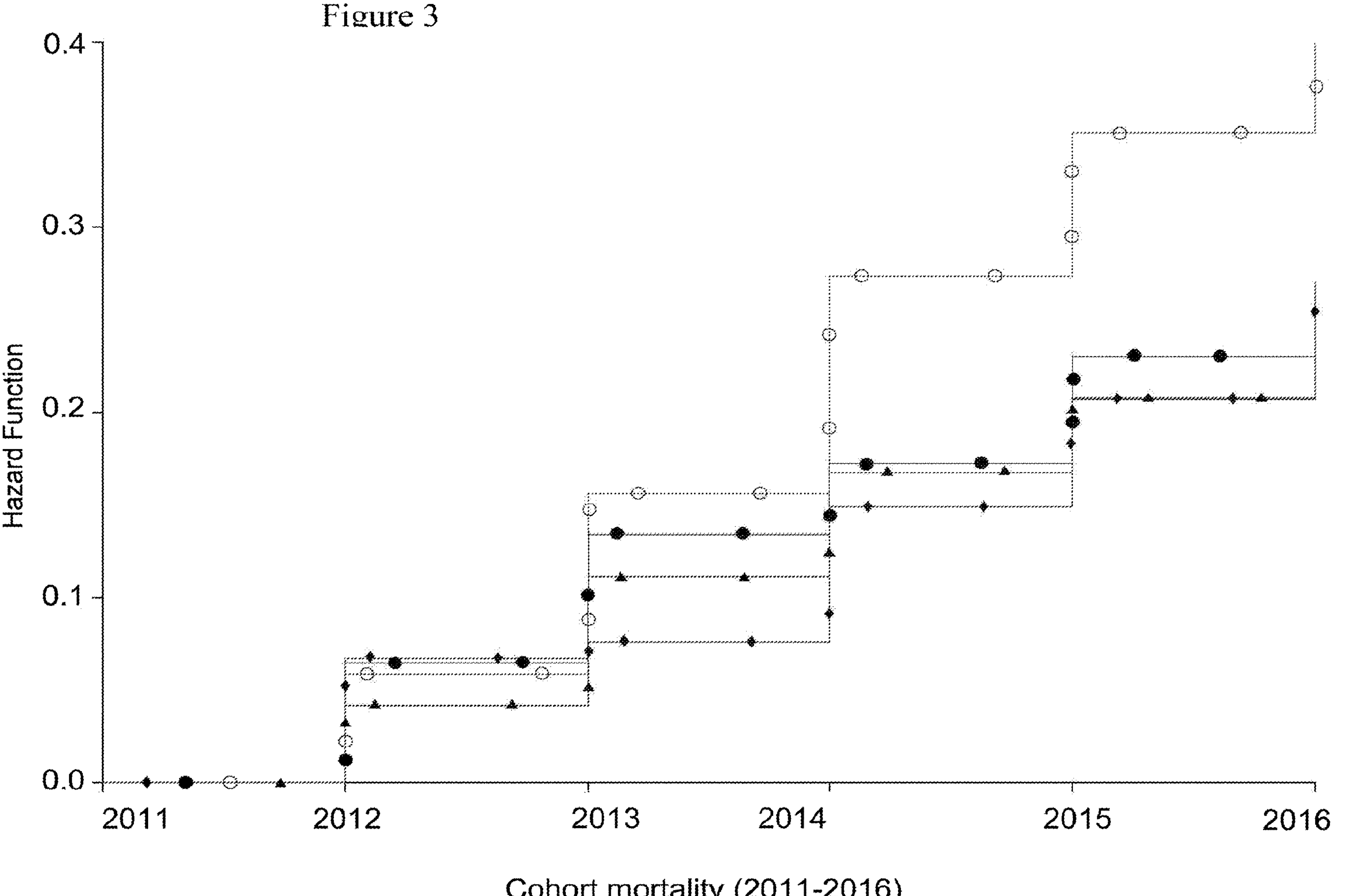
FIG. 3 presents a graph showing five-year mortality of the study cohort according to baseline plasma gelsolin levels measured at the beginning of the study. Gelsolin levels are shown as quartiles, from the lowest levels in the first quartile (Q1, indicated with open circles) to the highest levels in the fourth quartile (Q4, indicated with diamonds). Values obtained in the study are shown in Table 1. Q2 is indicated with triangles and Q3 is indicated with closed circles. By the third year of the study, mortality in Q1 had diverged from mortality in Q2-Q4.

Kaplan-Meier curves of 5-year total mortality are shown in FIGS. 2 and 3. There was a graded and highly significant (log-rank P<0.0001) association between frailty status at baseline and mortality (FIG. 2). In contrast, there was no significant difference (log-rank P=0.10) between all gelsolin quartiles and mortality (FIG. 3), but the lowest quartile was associated with highest mortality risk. Therefore, gelsolin levels were dichotomized for Cox analyses, and lowest quartile was compared with higher quartiles combined. Adjusted for age, the lowest quartile was associated with a 66% higher mortality risk (HR 1.66, 95% CI 1.14-2.42). The association prevailed even in the fully adjusted model with age, LDL-cholesterol, prealbumin, PEF, walk speed, and frailty index as covariates (HR 1.68, 95% CI 1.11-2.55).

Finally, the associations between various variables with frailty index were tested in the cohort. Only lower LDL-cholesterol and slower walk speed were associated with higher frailty index, no association was observed between plasma gelsolin and frailty index.

Discussion

In this octogenarian, home-dwelling male cohort, lower plasma gelsolin levels strongly and independently correlated with phenotypic frailty, but not prefrailty. Moreover, the lowest quartile of plasma gelsolin levels predicted total mortality during a 5-year follow-up. Frailty index did not correlate with plasma gelsolin concentrations.

Sarcopenia is a condition that frequent co-exists with frailty, but while all sarcopenic individuals are frail, not all frail persons are sarcopenic. Although sarcopenia was not directly measured in the present study, body composition measurements were performed in a random subcohort of the 87 men in this study, and among them gelsolin was significantly correlated with lean body mass ($r=0.29$, $P=0.006$). In contrast, there was no significant correlation between the frailty index and lean body mass ($r=-0.11$, $P=0.33$).

No previous studies have measured plasma gelsolin levels in frail individuals. Therefore, these results should stimulate more studies on gelsolin and frailty, because reliable molecular indicators of phenotypic frailty for clinical use are currently lacking. It is noteworthy that in this cohort, the association between plasma gelsolin and frailty was independent of walk speed or handgrip strength, which are well-known clinical markers of frailty.

The plasma concentrations of gelsolin in the subjects of this cohort were lower than the generally reported 190-300 μg/ml [See for example: Osborn T M, et al., (2008) Arthritis Research & Therapy 10(5):R117; Lee P-S, et al., (2008) PLOS One 3:11, 3712; Lee P-S. & Stossel T P. (2006) Annals of Surgery, 243(3):399-403; Kulakowska, A. et al., (2010) BMC Neurology 10:107; Kulakowska, A. et al., (2011) Neurodegenerative Dis. 8:375-380; and Lee P-S, et al., (2009) J. American Society of Nephrology: JASN. 20(5):1140-8.] While not desiring to be bound by any particular theory, it may not be possible to obtain reference values in octogenarians without serious, acute disease. Moreover, the distribution of gelsolin was not skewed in the instant cohort, suggesting that comparison between frailty groups is not biased.

The definition of phenotypic frailty using modified phenotypic criteria has proven predictive validity [Sirola J, et al., (2011) J Nutr Health Aging. 15:783-787], and is significantly correlated with walk speed and muscle strength. The area under the curve was not especially high (0.67) for gelsolin alone (FIG. 1), but studies are needed to develop a frailty score including gelsolin as an important component. Although the study cohort is homogenous, a person having ordinary skill in the art will recognize that an advantage of a homogenous cohort is the lack of confounding variables, and that the demonstrated predictive validity of the modified phenotypic criteria used in this study and the significant correlation between low pGSN levels and mortality risk is applicable to other types of cohorts.

Although the results of this study suggest that gelsolin depletion reflects frailty as a sarcopenic condition rather than as a condition of accumulated deficits reflected in the frailty index, the common denominator may be inflammation that clearly contributes to sarcopenia, and studies have documented elevated inflammation markers in frail individuals (Soysal, et al., (2016) Ageing Res Rev, 3: p. 1-8). Because gelsolin replacement therapy has improved outcomes in both acute [Peddada, N., et al., Plasma gelsolin: a general prognostic marker of health. Med Hypotheses, 2012. 78: p. 203-210] and chronic [Gupta, A., et al., (2015) PLoS One, 10: p. 0135558; and Kaneva, M., et al., (2017) J Immunol, 7: p. 2876-2885] inflammatory states associated with reduced plasma gelsolin levels, a therapeutic benefit of such treatment in frailty and sarcopenia might be warranted.

The results obtained in this study indicate plasma gelsolin is a promising molecular indicator for phenotypic frailty and sarcopenia.

Example 2—Treating Aging-Related Frailty

As described in the methods of Example 1, a 75 year-old subject undergoes a physical examination and measurements and responds to a questionnaire evaluating physical weakness, exhaustion, and physical inactivity. The subject presents with three frailty characteristics, leading to a phenotypic diagnosis of frailty. A therapeutic amount of a gelsolin agent is administered on an ongoing, regular basis to treat the subject's frailty condition. The status of the subject's frailty condition is monitored, including plasma gelsolin levels. Following 1 month of treatment with a therapeutic amount of gelsolin agent, the subject shows reduced physical weakness and reduced exhaustion, and is not presenting four frailty characteristics.

Example 3—Treating Aging-Related Frailty

As described in the methods of Example 1, an 85 year-old subject undergoes a physical examination and measurements and responds to a questionnaire evaluating physical weakness, exhaustion, and physical inactivity. The subject presents with three frailty characteristics, leading to a phenotypic diagnosis of frailty. A blood test is further administered to measure the subject's plasma gelsolin level. The subject's gelsolin level is 50 μg/ml, indicating the subject is at increased risk of mortality compared to a control risk. A therapeutic amount of a gelsolin agent is administered on a regular basis to treat the subject's frailty condition. The status of the subject's frailty condition is monitored, including plasma gelsolin levels. After one month of treatment with a therapeutic amount of gelsolin agent, the subject shows reduced physical weakness and reduced exhaustion, is not presenting four frailty characteristics, and does not die.

Example 4—Treating Non-Aging Related Frailty

A 50 year-old subject undergoes a physical examination and measurements and responds to a questionnaire evaluating physical weakness, exhaustion, and physical inactivity according to the methods of Example 1. The subject presents two frailty characteristics, leading to a phenotypic diagnosis of prefrailty. A therapeutic amount of a gelsolin agent is administered on a periodic basis to treat the subject's frailty condition. The status of the subject's frailty condition is monitored, including plasma gelsolin levels. After a one month treatment with a therapeutic amount of gelsolin agent, the subject presents one frailty characteristic instead of two.

Example 5—Treating Non-Aging Related Frailty

A 50 year-old subject undergoes a physical examination and measurements and responds to a questionnaire evaluating physical weakness, exhaustion, and physical inactivity according to the methods of Example 1. The subject presents two frailty characteristics, leading to a phenotypic diagnosis of prefrailty. A blood test is further administered to measure the subject's plasma gelsolin level. The subject's gelsolin level is 50 μg/ml, indicating that a diagnosis of frailty may be more accurate and that the subject is at increased risk of mortality. A therapeutic amount of a gelsolin agent is administered on a periodic basis to treat the subject's frailty condition. The status of the subject's frailty condition is monitored, including plasma gelsolin levels. After a one month treatment with a therapeutic amount of gelsolin agent, the subject does not experience mortality and presents one frailty characteristic instead of two.

Example 6—Seven-Year Mortality Follow-Up Studies

As a follow-up to the studies described in Example 1, additional analyses were performed on data from the Helsinki Businessmen Study for relationships with frailty phenotype and seven-year mortality. Plasma gelsolin concentrations in 2010/11 and seven years later in the cohort survivors showed a significant correlation with mortality and the relationship with frailty phenotype was replicated.

Methods

Methods were performed as described in Example 1, except as indicated below.

Participants

Survivors responded to questionnaire surveys in 2000, 2010, and 2017. In 2010/11 and 2017, prefrailty and frailty phenotypes were assessed clinically in a random subcohort of 525 individuals (mean age 83), and laboratory measurements included plasma gelsolin (n=505). Mortality through Dec. 31, 2018 was retrieved from national registers.

Clinical and Laboratory Investigations

Samples were taken and clinical and laboratory tests were performed as described in Example 1. In 2017, the questionnaire, clinical, and laboratory examinations, including plasma gelsolin analysis, were repeated as described in Example 1 for 127 survivors of the Helsinki Businessmen Study (HBS). Weight-adjusted waist index, reflecting fat and muscle mass, was calculated as previously described [Kim, N. H. et al., Age Ageing afaa208 (2020)]. Frailty phenotype was defined as in 2010/11 and used the same cut-off points.

Frailty Assessment

Robust, prefrail, and frail phenotypes were defined as described in Example 1, according to the following phenotypic criteria: (1) shrinking: weight loss (>5% from 2000, or current BMI <18.5 kg/$m^2$); (2) weakness: hand grip strength (cut-off point 27 kg) [Ha Y. C. et al., Eur Geriatr Med. 9, 277-288 (2018)]; (3) exhaustion (reported low energy most or all of the time during the preceding four weeks; one of the questions of the Vitality domain of RAND-36); (4) low activity (based on the question: "Do you exercise regularly weekly?"; a "no" response was taken to denote low physical activity); and (5) slowness (walk speed <0.8 m/s) [Studenski S. et al., Responders with 3-5, 1-2, and zero criteria were classified as frail, prefrail, and robust, respectively. In the 2017 examinations, frailty status was defined as described herein, except that weight loss was calculated from weight measured in 2010/11.

Mortality

Participants were linked to electronic health records of the Digital and Population Data Services Agency (dvv.fi), which keeps a registry of all Finnish citizens thus permitting reliable determination of vital status. Total mortality of the study cohort was retrieved through Dec. 31, 2018.

Gelsolin Analysis

Plasma gelsolin from frozen samples was measured by as indicated in Example 1, by BioAegis Therapeutics, Inc (North Brunswick, N.J.) and as described above herein. The assays were performed in a blind manner with laboratory personnel who performed the assay unaware of the clinical outcomes.

Statistical Analysis

Statistical analyses of relationships with frailty phenotype and 7-year mortality were performed with NCSS 2020 software (NCSS, Kaysville, Utah). Continuous variables are shown as means with standard deviations (SD) or standard error (SE), or medians with interquartile ranges (IQR). Spearman rank correlation and analysis of covariance (ANCOVA) were used to compare groups. Logistic regression was used to examine associations of gelsolin and other baseline covariates with frailty and prefrailty. Covariates were clinically meaningful variables which in univariate analyses were significantly related to frailty phenotype ($p<0.05$). Gelsolin was studied both as a continuous variable and as divided into thirds with the bottom tertile as the reference. The results are presented as odds ratios (OR) with their 95% confidence intervals (CI).

After confirming that the proportional hazards assumption was met, predictors of seven-year mortality were examined using Cox proportional hazards models. Results are presented as hazard ratios (HR) with their 95% CIs. Effect estimates were adjusted for the same covariates as in the analysis of frailty. Receiver operating curves (ROC) were constructed for gelsolin, frailty, and mortality. In all analyses, p values of less than 0.05 (two-sided) were considered to indicate statistical significance.

Results

Of the 525 men (mean age 82.8 years, median 82, IQR 80-85), 190 (36.2%) were assessed to be robust, 284 (54.1%) were assessed to be prefrail, and 51 (9.7%) were assessed to be frail. Baseline characteristics of the study cohort are shown in Table 3 according to frailty groups. Among clinical characteristics measured, as expected, those related to frailty phenotype (walk speed, grip strength, PEF) were lower, while the reported number of falls during the previous year was higher among frail men. During the seven-year follow-up, 225 men died and the frailty phenotype was significantly ($p<0.001$) associated with mortality risk (Table 3). While BMI was similar among the groups, waist circumference and weight-adjusted waist were higher in prefrail and frail men than in robust men. Of the laboratory variables measured, only higher plasma homocysteine differentiated robust men from prefrail and frail men (p=0.01). High-sensitivity C-reactive protein concentration and lipid values were not different between frailty groups.

TABLE 3

Age-adjusted characteristics according to frailty phenotype at baseline in 2011

| Variable* | All, n = 525 | Robust n = 190 (36.2%) | Prefrail n = 284 (54.1%) | Frail, n = 51 (9.7%) | p-value for linear trend between frailty groups |
|---|---|---|---|---|---|
| Age, yr | 83.3 (0.2) | 81.8 (0.3) | 83.0 (0.2) | 85.0 (0.5) | 0.00001 |
| BMI, kg/$m^2$ | 25.0 (0.2) | 24.8 (0.2) | 25.1 (0.2) | 25.0 (0.4) | 0.60 |
| Waist circumference, cm | 97.1 (2.6) | 95.5 (2.9) | 97.9 (2.5) | 97.8 (5.3) | 0.027 |

TABLE 3-continued

| Age-adjusted characteristics according to frailty phenotype at baseline in 2011 | | | | | |
|---|---|---|---|---|---|
| Variable* | All, n = 525 | Robust n = 190 (36.2%) | Prefrail n = 284 (54.1%) | Frail, n = 51 (9.7%) | p-value for linear trend between frailty groups |
| Weight-adjusted waist index | 11.0 (0.04) | 10.8 (0.05) | 11.0 (0.04) | 11.1 (0.09) | 0.004 |
| Smokers, n = 19, % | 3.9 | 4.0 | 3.0 | 8.3 | 0.22 |
| Plasma gel solin, ug/mL (n = 505) | 57.3 (0.6) | 59.3 (0.7) | 58.0 (0.6) | 54.5 (1.2) | 0.009 |
| Plasma lipids, mmol/L | | | | | |
| cholesterol | 4.8 (0.07) | 4.8 (0.08) | 4.8 (0.06) | 4.8 (0.1) | 0.83 |
| HDL cholesterol | 1.5 (0.03) | 1.5 (0.03) | 1.5 (0.03) | 1.5 (0.06) | 0.92 |
| LDL cholesterol | 2.7 (0.05) | 2.7 (0.06) | 2.7 (0.05) | 2.7 (0.1) | 0.60 |
| trigycerides | 1.29 (0.04) | 1.29 (0.05) | 1.27 (0.04) | 1.30 (0.09) | 0.93 |
| Plasma glucose, mmol/L | 5.8 (0.09) | 5.9 (0.1) | 5.8 (0.09) | 5.8 (0.2) | 0.88 |
| Plasma insulin | 14.4 (0.9) | 13.5 (1.1) | 14.7 (0.9) | 15.0 (2.0) | 0.68 |
| Plasma urate | 383.7 (6.1) | 379.5 (6.5) | 384.9 (5.6) | 386.7 (12.6) | 0.80 |
| Prealbumin | 0.25 (0.003) | 0.25 (0.003) | 0.25 (0.003) | 0.26 (0.006) | 0.74 |
| hs C-reactive protein | 2.4 (0.4) | 2.2 (0.5) | 3.1 (0.4) | 1.9 (0.8) | 0.23 (log) |
| Creatinine | 96.1 (2.0) | 95.1 (2.3) | 99.6 (2.0) | 93.5 (4.2) | 0.19 |
| ALT | 18.4 (0.5) | 1910 (0.6) | 18.6 (0.5) | 17.5 (1.1) | 0.46 |
| Homocysteine | 15.7 (0.4) | 15.0 (0.4) | 16.4 (0.3) | 15.8 (0.7) | 0.015 |
| PEF | 430.0 (6.0) | 461.7 (6.5) | 432.7 (5.6) | 395.5 (12.7) | 0.0001 |
| MMSE, points | 28.1 (0.2) | 28.4 (0.2) | 28.1 (0.1) | 27.8 (0.3) | 0.17 |
| Walk speed, m/s | 0.81 (0.01) | 0.97 (0.01) | 0.80 (0.01) | 0.68 (0.02) | 0.0001 |
| Grip strength | 35.0 (0.7) | 38.8 (0.7) | 36.8 (0.6) | 29.3 (1.3) | 0.0001 |
| 7-year mortality, n, % | 229 (43.6) | 53 (27.9) | 137 (48.2) | 39 (76.5) | 0.0001 |
| No reported falls during past year n, % | 336 (69.9) | 135 (78.0) | 183 (67.2) | 28 (57.1) | 0.014 |

Notes:
BMI = body mass index;
*Age-adjusted, continuous variables are mean (SE).
Log-transformed values where used where indicated.

Mean plasma gelsolin in the cohort was 58.1 μg/mL (SD 9.3) and median 57.8 μg/mL (IQR 52.2 to 63.9) and followed a Gaussian distribution. There was a graded and statistically significant (p=0.009) association between frailty status and plasma gelsolin, with robust men having the highest plasma gelsolin values (Table 3). After adjustment for age, waist circumference, PEF, and homocysteine, a 1 SD higher plasma gelsolin level was associated with a 9% lower odds of prefrailty phenotype (p=0.37) and a 34% lower odds of frailty phenotype (p=0.032, Table 4).

TABLE 4

| Odds ratios of prefrailty and frailty phenotype according to plasma gelsolin concentration (N = 505) | | |
|---|---|---|
| | Odds ratio 95% Confidence Interval (CI) per 1 SD increase in plasma gelsolin | |
| Adjustment | Prefrail n = 273 | Frail n = 49 |
| Unadjusted | 0.90 (0.74-1.08) | 0.63 (0.46-0.88) |
| Age | 0.87 (0.72-1.06) | 0.58 (0.41-0.82) |
| Age, waist circumference, PEF and homocysteine, | 0.91 (0.73-1.12) | 0.66 (0.45-0.96) |

Figure 4:
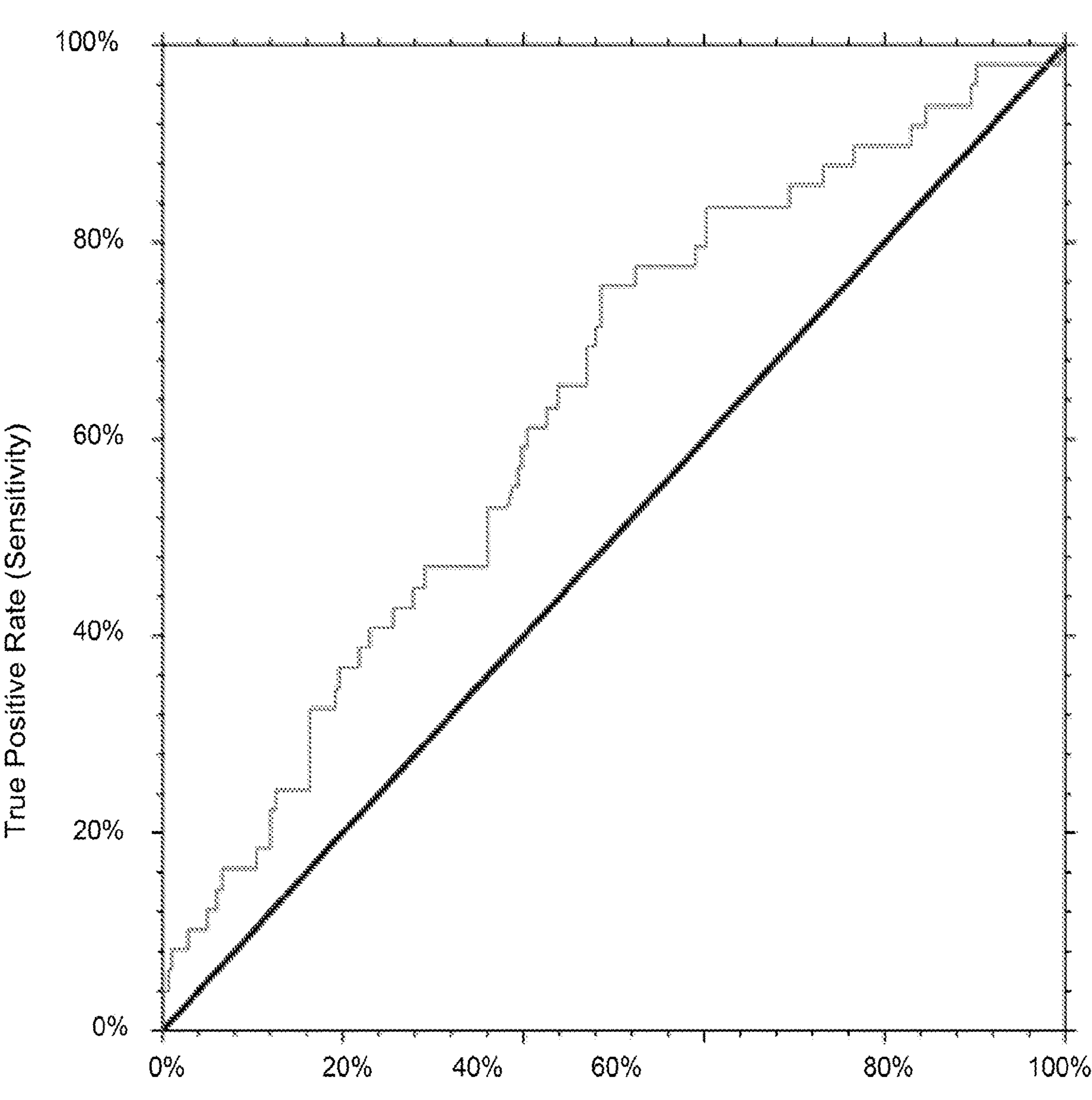
FIG. 4 presents a graph showing receiver operating characteristic (ROC) curves between gelsolin and frailty.

Odds of frailty were also compared according to tertiles of gelsolin concentration (Table 5). In a model adjusted for age, homocysteine, and frailty index and bottom tertile as referent, the top tertile was associated with a 74% lower odds of frailty phenotype. Area under the curve for gelsolin and frailty was 0.63 (95% CI 0.54-0.71) (FIG. 4).

TABLE 5

| Odds ratios of prefrailty and frailty phenotype in old age according to plasma gelsolin tertiles (N = 505) | | | |
|---|---|---|---|
| | | Odds ratio (95% confidence interval) | |
| Gelsolin tertiles | N (cases) | Model 1* | Model 2† |
| | | Outcome: Prefrailty | |
| Bottom | 165 (95) | 1.00 (reference) | 1.00 (reference) |
| Intermediate | 178 (88) | 0.67 (0.42-1.08) | 0.64 (0.38-1.05) |
| Top | 162 (90) | 0.68 (0.42-1.10) | 0.67 (0.40-1.13) |
| | | Outcome: Frailty | |
| Bottom | 165 (21) | 1.00 (reference) | 1.00 (reference) |
| Intermediate | 178 (20) | 0.71 (0.34-1.50) | 0.58 (0.25-1.33) |
| Top | 162 (8) | 0.24 (0.09-0.60) | 0.26 (0.10-0.72) |

*Adjusted for age.
†Adjusted for age, waist circumference, homocysteine, and PEF.

During the seven-year follow-up, higher plasma gelsolin, both as a continuous (per SD) and as a categorical variable in tertiles, was associated with a significantly lower risk of mortality (Table 6). Higher plasma gelsolin concentration predicted mortality independently of walk speed (HR per 1SD 0.68, 95% CI 0.48-0.96).

TABLE 6

Hazards ratios of seven-year mortality according to plasma gelsolin among older males (N = 505)

| | N (dead) | Hazards ratio (95% confidence interval) Outcome: Mortality Model 1* | Model 2† |
|---|---|---|---|
| Gel solin, continuous per SD | | | |
| | 521 (225) | 0.81 (0.70-0.93) | 0.77 (0.60-0.90) |
| Gelsolin tertiles | | | |
| Bottom | 173 (90) | 1.00 (reference) | 1.00 (reference) |
| Intermediate | 183 (73) | 0.72 (0.52-0.99) | 0.71 (0.50-1.01) |
| Top | 165 (64) | 0.60 (0.44-0.95) | 0.57 (0.40-0.82) |

*Adjusted for age.

†Adjusted for age, waist circumference, PEF and homocysteine.

In the 2017 examination of 127 surviving men (mean age 88 years, SD 2.7), 26 (20.5%) were robust, 81 (63.8%) prefrail, and 20 (15.8%) frail. Plasma gelsolin concentrations in 2010/11 and 2017 were correlated ($r=0.35$, $p<0.001$), but mean concentration in 2017 (63.0 μg/ml) was higher than in 2010/11 (57.3 μg/ml). Mean age-adjusted gelsolin concentration was 67.2 μg/ml in robust and 58.9 μg/ml in frail men ($p=0.028$). In age-adjusted analyses, higher plasma gelsolin concentration was associated with a 57% lower odds of frailty (OR per 1SD 0.43, 95% CI 0.20-0.91).

Discussion

In this octogenarian, home-dwelling male cohort, higher plasma gelsolin level was associated with a robust phenotype independently of other clinical characteristics, and also predicted lower total mortality over seven years of follow-up. The association between plasma gelsolin and frailty phenotype described in Example 1 was replicated in a small group of survivors in this seven-year follow-up study. Among a large set of laboratory variables, including high-sensitivity C-reactive protein, gelsolin was the strongest indicator for the frailty phenotype.

The robust association between low gelsolin and frailty was important, because reliable indicators of phenotypic frailty for clinical use are currently lacking. In the study cohort, the association between plasma gelsolin and frailty was also independent of walk speed, which is a widely used clinical marker of frailty [Studenski S. et al., JAMA 305(1), 50-58 (2011)]. The prognostic value of the modified frailty phenotype criteria as described herein and in Example 1 was also validated in the cohort in this study. Because plasma gelsolin mainly originates from myocytes, results of the studies described herein support a conclusion that gelsolin reflects frailty as a sarcopenic condition [Patel, S. S. et al., J. Cachexia Sarcopenia Muscle 4:19 (2013)]. Sarcopenia is a frequent co-existing condition with frailty, but while all sarcopenic individuals are more or less frail, all frail persons are not sarcopenic. The studies herein did not directly measure sarcopenia, however, in-body measurements of body composition were performed for a random subcohort of 87 men, and among them gelsolin was significantly correlated with lean body mass ($r=0.29$, $P=0.006$).

There are no general reference values for plasma gelsolin in the population. The plasma concentrations of gelsolin in this cohort showed a Gaussian distribution, but were lower than the 190-300 μg/ml values reported in some patient series [Feldt J. et al., Rev Molec Med (2019) 20, e7] and higher than in acute pneumonia patients [Self W. H. et al., Clin Infect Dis. 69(7): 1218-1225 (2019). In a small series of surgical patients, plasma gelsolin concentration below 61 μg/ml was associated with increased mortality risk [Lee P. S. et al., Ann Surg. 243, 399-403 (2006)]. The origin of plasma gelsolin from muscle and increasing prevalence of sarcopenia with age, supports a finding that concentrations generally decrease with age. That concentrations did not materially change during the seven-year follow-up may be explained by selection: only better-functioning survivors were alive and able to participate in clinic examinations at a mean age of 88 years.

Although the study cohort was homogenous, one with ordinary skill in the art will recognize that an advantage of a homogenous cohort is the lack of confounding variables, and that the demonstrated predictive validity of the modified phenotypic criteria used in this study and the significant correlation between pGSN levels and mortality risk is applicable to other types of cohorts. Gelsolin values in this cohort were higher than concentrations in severe diseases probably reflecting relatively high functional status of the participants (only half with frailty phenotype were frail according to frailty index, unpublished observations). The area under the curve was relatively high (0.63, FIG. 4) considering that gelsolin was used as a single indicator of a multi-factorial frailty phenotype. The results of this study supports a conclusion that plasma gelsolin levels predict long-term mortality among octogenarians and can be used as an indicator for phenotypic frailty and sarcopenia.

EQUIVALENTS

It is to be understood that the methods and compositions that have been described above are merely illustrative applications of the principles of the invention. Numerous modifications may be made by those skilled in the art without departing from the scope of the invention. Although the invention has been described in detail for the purpose of illustration, it is understood that such detail is solely for that purpose and variations can be made by those skilled in the art without departing from the spirit and scope of the invention which is defined by the following claims.

The contents of all literature references, publications, patents, and published patent applications cited throughout this application are incorporated herein by reference in their entirety.

What is claimed is:

1. A method for treating a phenotypic frailty or prefrailty condition in a subject exhibiting two or more frailty characteristics selected from the group consisting of physical weakness, exhaustion, and physical inactivity, the method comprising administering to the subject an effective amount of a gelsolin molecule to treat the phenotypic frailty or prefrailty condition in the subject.

2. The method of claim 1, wherein the subject exhibits physical weakness, exhaustion, and physical inactivity.

3. The method of claim 1, further comprising determining a status of at least one of the two or more frailty characteristics exhibited by the subject.

4. The method of claim 3, wherein the status of the at least one of the two or more frailty characteristics is determined at 1, 2, 3, 4, 5, 6, 7, 8, 9, 10, or more different time points.

5. The method of claim 3, wherein the status of the at least one of the two or more frailty characteristics is determined at one or more of:

(1) a time prior to administering the gelsolin molecule; and (2) a time after administering the gelsolin molecule.

6. The method of claim 3, further comprising comparing the status of the at least one of the two or more frailty characteristics exhibited by the subject with a control status of the at least one of the two or more frailty characteristics, respectively, wherein the control status is that of the at least one of the two or more frailty characteristics exhibited by the subject prior to administering the gelsolin molecule, and an improvement in the status of at least one of the two or more frailty characteristics in the subject compared to the control status of the characteristic, indicates effectiveness of the administered gelsolin molecule in the subject.

7. The method of claim 1, wherein administering the gelsolin molecule increases the subject's likelihood of survival compared to a control likelihood of survival, wherein the control likelihood of survival is that of a subject with the phenotypic frailty or prefrailty condition in the absence of administering the gelsolin molecule.

8. The method of claim 1, wherein the subject has one or more symptoms of:

muscle wasting, cachexia, physical injury, impaired locomotion, and decreased physical stability.

9. The method of claim 1, further comprising determining a status of one or more of: muscle wasting, cachexia, physical injury, impaired locomotion, and physical stability in the subject.

10. The method of claim 1, wherein the phenotypic frailty or prefrailty condition is an age-related frailty condition.

11. The method of claim 1, wherein the gelsolin molecule is a plasma gelsolin (pGSN).

12. The method of claim 1, wherein the gelsolin molecule is a recombinant gelsolin molecule.

13. The method of claim 1, wherein the subject is at least 60 years old.

14. The method of claim 9, wherein the status is determined at 1, 2, 3, 4, 5, 6, 7, 8, 9, 10, or more different time points and wherein the status is determined at one or more of:

(1) a time prior to administering the gelsolin molecule; and (2) a time after administering the gelsolin molecule.

15. The method of claim 9, wherein administering the gelsolin molecule to the subject improves the status of one or more of muscle wasting, cachexia, physical injury, impaired locomotion, and physical stability in the subject compared to a control status of muscle wasting, cachexia, physical injury, impaired locomotion, and physical stability, respectively.

16. The method of claim 1, wherein the subject is a mammal.

* * * * *